(12) United States Patent
Martin et al.

(10) Patent No.: US 6,315,741 B1
(45) Date of Patent: Nov. 13, 2001

(54) METHOD AND APPARATUS FOR MEDICAL PROCEDURES USING HIGH-INTENSITY FOCUSED ULTRASOUND

(76) Inventors: Roy W. Martin, Box 356540, Univ. of Washington; Lawrence A. Crum, Box 355640, Univ. of Washington; Shahram Vaezy, Box 357420, HSB R.R. 411, Univ. of Washington; Stephen J. Carter, Box 357115, Univ. of Washington; W. Scott Helton; Michael Gaps, both of Box 356410, Univ. of Washington; Peter J. Kaczkowski; Andrew Proctor, both of Box 355640, Univ. of Washington, all of Seattle, WA (US) 98195; George Keilman, 20018 163rd Ave. NE., Woodinville, WA (US) 98072

( * ) Notice: Subject to any disclaimer, the term of this patent is extended or adjusted under 35 U.S.C. 154(b) by 0 days.

(21) Appl. No.: 09/390,506

(22) Filed: Sep. 3, 1999

Related U.S. Application Data

(62) Division of application No. 08/961,972, filed on Oct. 31, 1997, now Pat. No. 6,007,499.

(51) Int. Cl.[7] .................................................. A61B 17/22
(52) U.S. Cl. .............................................................. 601/3
(58) Field of Search ........................... 301/2–4; 600/439, 600/454, 411, 427, 447, 457, 455, 459, 461, 371

(56) References Cited

U.S. PATENT DOCUMENTS

| 4,363,326 | * | 12/1982 | Kopel ..................................... 600/439 |
| 5,676,692 | * | 10/1997 | Sanghvi et al. ....................... 607/105 |
| 5,762,066 | * | 6/1998 | Law et al. ................................. 601/3 |
| 5,873,828 | * | 2/1999 | Fujio et al. ........................... 600/439 |
| 5,897,503 | * | 4/1999 | Lyon et al. ............................ 600/459 |
| 6,083,159 | * | 7/2000 | Driscoll, Jr. et al. ................. 600/371 |
| 6,086,535 | * | 7/2000 | Ishibashi et al. ..................... 600/439 |

* cited by examiner

*Primary Examiner*—Brian L. Casler
(74) *Attorney, Agent, or Firm*—Eugene H. Valet

(57) ABSTRACT

Methods and apparatus for enabling substantially bloodless surgery and for stemming hemorrhaging. High intensity focused ultrasound ("HIFU") is used to form cauterized tissue regions prior to surgical incision, for example, forming a cauterized tissue shell around a tumor to be removed. The procedure is referred to as "presurgical volume cauterization." In one embodiment, the method is particularly effective for use in surgical lesion removal or resection of tissue having a highly vascularized constitution, such as the liver or spleen, and thus a propensity for hemorrhaging. In further embodiments, methods and apparatus for hemostasis using HIFU is useful in both surgical, presurgical, and medical emergency situations. In an apparatus embodiment, a telescoping, acoustic coupler is provided such that depth of focus of the HIFU energy is controllable. In other embodiments, apparatus characterized by portability are demonstrated, useful for emergency medical situations.

8 Claims, 18 Drawing Sheets

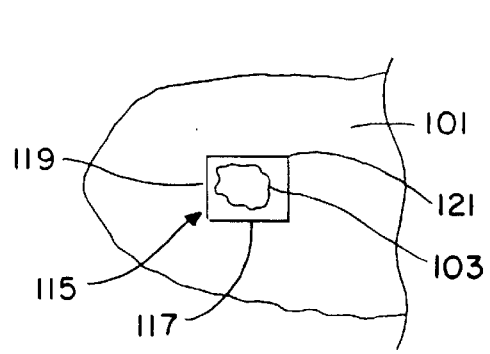
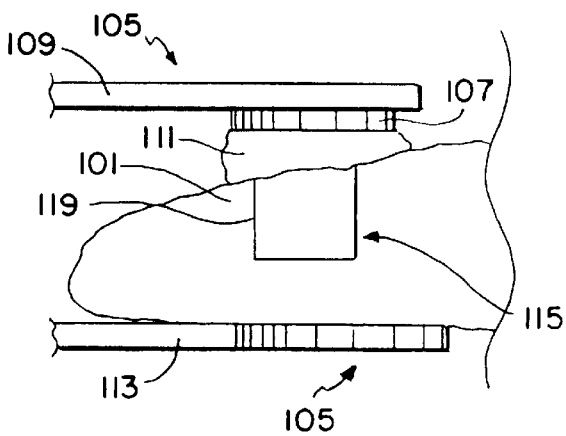
FIG. 1A
FIG. 1B
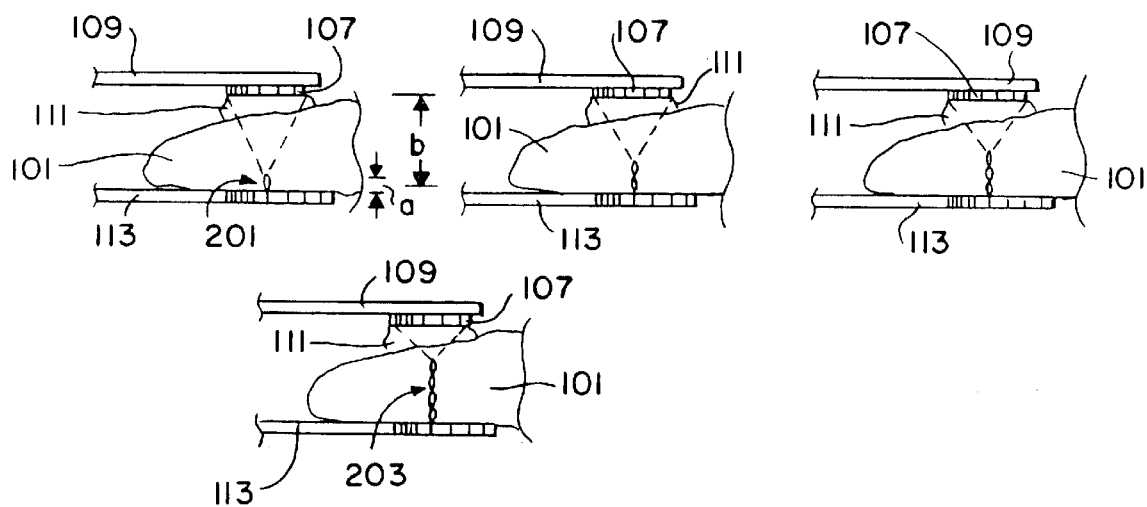
FIG. 2A    FIG. 2B    FIG. 2C
FIG. 2D

METHOD AND APPARATUS FOR MEDICAL PROCEDURES USING HIGH-INTENSITY FOCUSED ULTRASOUND

This application is a division of application Ser. No. 08/961,972, filed Oct. 31, 1997, now U.S. Pat. No. 6,007,499.

The invention described herein was made in the course of work under a grant or award from the U.S. Department of Defense, Office of Naval Research.

BACKGROUND OF THE INVENTION

1. Field of the Invention

The present invention relates generally to uses of ultrasonics in medical technology applications, more particularly to a method and apparatus for performing presurgical and surgical procedures using high-intensity focused ultrasound.

2. Description of Related Art

Studies in the use of ultrasound—sound with frequency above 20,000 Hz, the upper limit of human hearing—began in the early 1940's [see e.g., A New Method for the Generation and Use of Focused Ultrasound in Experimental Biology, Lynn et al., Focused Ultrasound in Experimental Biology, Journal of General Physiology, 1943, pp. 179–193]. It is widely accepted that the first refined system for the use of ultrasound in the medical arts was developed by William and Francis Fry at the University of Illinois, Urbana, in the 1950's (a paper was published as part of the Scientific Program of the Third Annual Conference of the American Institute of Ultrasonics in Medicine, Washington D.C., Sep. 4,1954, pp. 413–423).

In the main, research and development has been concerned with diagnostic and therapeutic applications. Therapeutic ultrasound refers to the use of high intensity ultrasonic waves to induce changes in tissue state through both thermal effects—induced hyperthermia—and mechanical effects—induced cavitation. High frequency ultrasound has been employed in both hyper-thermic and cavitational medical applications, whereas low frequency ultrasound has been used principally for its cavitation effect. Diagnostic medical ultrasonic imaging is well known, for example, in the common use of sonograms for fetal examination.

Various aspects of diagnostic and therapeutic ultrasound methodologies and apparatus are discussed in depth in an article by G. ter Haar, Ultrasound Focal Beam Surgery, Ultrasound in Med. & Biol., Vol. 21, No. 9, pp. 1089–1100, 1995, and the *IEEE Transactions on Ultrasonics, Ferroelectrics, and Frequency Control,* November 1996, Vol. 43, No. 6 (ISSN 0885-3010). The IEEE journal is quick to point out that: "The basic principles of thermal effects are well understood, but work is still needed to establish thresholds for damage, dose effects, and transducer characteristics . . . " Id., Introduction , at page 990.

In high-intensity focused ultrasound (HIFU) hyperthermia treatments, intensity of ultrasonic waves generated by a highly focused transducer increases from the source to the region of focus where it can reach a very high temperature, e.g. 98° Centigrade. The absorption of the ultrasonic energy at the focus induces a sudden temperature rise of tissue—as high as one to two hundred degrees Kelvin/second—which causes the irreversible ablation of the target volume of cells, the focal region. Thus, for example, HIFU hyperthermia treatments can cause necrotization of an internal lesion without damage to the intermediate tissues. The focal region dimensions are referred to as the depth of field, and the distance from the transducer to the center point of the focal region is referred to as the depth of focus. In the main, ultrasound is a promising non-invasive surgical technique because the ultrasonic waves provide a non-effective penetration of intervening tissues, yet with sufficiently low attenuation to deliver energy to a small focal target volume. Currently there is no other known modality that offers noninvasive, deep, localized focusing of non-ionizing radiation for therapeutic purposes. Thus, ultrasonic treatment has a great advantage over microwave and radioactive therapeutic treatment techniques.

A major issue facing the use of HIFU techniques is cavitation effects. In some quarters, it is recognized that cavitation can be used advantageously. See e.g., Enhancement of Sonodynamic Tissue Damage Production by Second-Harmonic Superimposition: Theoretical Analysis of Its Mechanism, Unmemura et al. IEEE Transactions on Ultrasonics, Ferroelectrics, and Frequency Control, Vol. 43, No. 6, November 1996 at page 1054. Cavitation can occur in at least three ways important for consideration in the use of ultrasound for medical procedures. The first is gaseous cavitation, where dissolved gas is pulled from solution during a negative pressure phase of an acoustic wave. The second is vaporous cavitation due to the negative pressure in the negative pressure phase becoming low enough for a fluid to convert to its vapor form at the ambient temperature of the tissue fluid. The third is where the ultrasonic energy is absorbed to an extent to raise the temperature above boiling at ambient pressure. At lower frequencies, the time that the wave is naturally in the negative pressure phase is longer than at higher frequencies, providing time for gas or vapor to come out of the fluid. All other factors being equal, a lower frequency will have a lower intensity level for cavitation than a higher frequency. Higher frequencies are more rapidly absorbed and therefore raise the temperature more rapidly for the same applied intensity than a lower frequency. Thus, gaseous and vaporous cavitation are promoted by low frequencies and boiling cavitation by high frequency.

For HIFU applications it has been found that ultrasonically induced cavitation occurs when an intensity threshold is exceeded such that tensile stresses produced by acoustic rarefaction generates vapor cavities within the tissue itself. Subsequent acoustic compressions drive the cavities into a violent, implosive collapse; because non-condensing gases are created, there are strong radiating pressure forces that exert high shear stresses. Consequently, the tissue can shred or be pureed into an essentially liquid state. Control of such effects has yet to be realized for practical purposes; hence, it is generally desirable to avoid tissue damaging cavitation whenever it is not a part of the intended treatment.

Another problem facing the designer of ultrasound medical devices is that the attenuation and absorption rate of ultrasound in tissue is known to exponentially increase in proportion to the frequency. In other words, a very high frequency, e.g., 30 MHz wave would be absorbed nearly immediately by the first tissue it is applied to. Yet, lower frequencies, e.g., 30 KHz–60 KHz, are associated with cavitation effects because of the longer rarefaction time periods, allowing gaseous vapor formation. Thus, the effect of ultrasound energy is quite different at a frequency of 30 KHz versus 30 MHz. The rate of heat generation in tissue is proportional to the absorption constant. For example, for the liver, the attenuation constant is approximately 0.0015 at 30 KHz, but is approximately 0.29 at 3 MHz. Therefore, all other variables being equal, the heat generated in liver tissue is about 190 times greater at 3 MHz than at 30 KHz. While this means hyperthermia can be achieved more quickly and to a much greater level with high frequencies, the danger to intervening tissue between the transducer and the focal region is much more prevalent.

Thus, there is a continuing need in the field for means of improving heating penetration, spatial localization, and dynamic control of ultrasound for medical applications, along with the discovery of new methodologies of their use.

An even less explored field of ultrasound use is as a direct surgical tool for non-invasive surgical procedures. While ultrasound has been used as a electromechanical driver for cutting tool implementations (see e.g., U.S. Pat. No. 5,324, 299 to Davison et al. for an ultrasonic scalpel blade, sometimes referred to as a "harmonic scalpel"), the use of ultrasonic radiation directly in a device for performing presurgical and surgical procedures, rather than therapeutic procedures, has been limited. An ultrasonic diagnostic and therapeutic transducer assembly and method of use for ophthalmic therapy is shown by Driller et al. in U.S. Pat. No. 4,484,569. The acoustic coupler in the Driller device is a fluid-filled, conical shell, mounted to a transducer apparatus and having a flexible membrane across the apertured, distal end of the cone. Depth of focus is controlled by changing the aperture size and the spacing from the focal point of a fixed focal point transducer by using cones of varying axial length. The problem with this construct is that the focal point is fixed and that the cones must be manually changed (compare Driller's FIG. 2 and FIG. 5).

During invasive surgery, an obvious primary problem is bleeding. The most common surgical technique in the state of the art for coagulating bleeding vessels is to apply an electrical cauterizing probe to the bleeding site (see, e.g., U.S. Pat. No. 4,886,060, to Wiksell for an ultrasonically driven, oscillating knife having a means for emitting high-frequency electrical energy which induces heat in the tissue). However, if a bleeding vessel is more than about 1.5 mm in diameter, or in an organ such as the liver, which is highly vascularized and where uncontrolled hemorrhage is the primary cause of death in hepatic trauma, direct electro-cauterization is ineffective. A more complicated technique of clamping of a large blood vessel and electrical cauterization via the clamp or with laser light can sometimes be effective. A major problem that is not solved with either electrical or laser cauterization techniques is the control of a rapidly bleeding vessel because the blood egress is often sufficiently large enough to carry the heat away before coagulation or tissue necrosis is accomplished. In liver surgery, neither is effective. Moreover, organs such as the liver and spleen are subject to bleeding profusely from cracks in the parenchyma, which is usually diffuse and non-pulsatile due to the large number of small vessels. In another example, the control of bleeding is the most important variable in determining the length of neurosurgical craniotomy procedures.

Another important application in need of technologically advanced medical treatment is for emergency hemorrhaging situations, e.g., an accidently severed femoral artery, massive internal bleeding, or puncture wounds due to bullets, knives, or automobile accidents. Prompt stemming of visible hemorrhaging is literally a matter of life or death. Standard procedure to arrest visible bleeding is to maintain pressure on the puncture site until coagulation is sufficient to stem the flow of blood. Without sophisticated hospital equipment and invasive surgery, the problem of internal bleeding lacks suitable emergency treatment devices.

The present invention meets the various needs in the field of technology by presenting a method and apparatus using high intensity focused ultrasound for inducing coagulative necrosis and hemostasis that can be used in presurgical procedures such that substantially bloodless surgery can be achieved. The present invention further provides methods and apparatus using high intensity focused ultrasound for stemming hemorrhaging in emergency situations or with organs where tradition methodologies are ineffective.

SUMMARY OF THE INVENTION

In its basic aspects, the present invention provides a method of performing surgery with minimized bleeding, including the steps of: determining each path of incision to be made in a tissue volume; cauterizing each path using ultrasonic energy to form at least one surgical pathway in the tissue volume prior to incising; and making surgical incisions only along a surgical pathway.

In another basic aspect, the present invention provides a method for presurgical treatment of highly vascularized organic tissue to minimize bleeding during surgical procedures including the steps of: determining each path of incision to be made in the tissue; and prior to incising the tissue, exposing each path to high intensity focused ultrasound energy having a predetermined frequency for a time period sufficient to form at least one coagulative necrosed pathway in the tissue such that making surgical incisions only along a coagulative necrosed pathway is subject to minimized bleeding.

In another basic aspect, the present invention provides a method for causing hemostasis including the steps of: exposing a hemorrhaging blood vessel or parenchyma; and exposing said blood vessel or parenchyma to sonic energy comprising high intensity focused ultrasound such that said hemorrhaging blood vessel or parenchyma is cauterized by said sonic energy.

In another basic aspect, the present invention provides a presurgical device for preparing an organ of a patient for surgical incisions. The device includes: a transducer mechanism for emitting energy as high frequency focused ultrasound; and a mechanism for controlling focal position and focal intensity of energy emissions from said transducer such that acoustic energy at selective focal zones produces coagulative necrosed tissue in the form of predetermined surgical pathways within the tissue such that surgical incisions along the surgical pathways is subject to substantially no bleeding. Various embodiments of devices are disclosed, including screw-type and bellows-type focusing apparatus.

In another basic aspect, the present invention provides a method for causing hemostasis in a visible hemorrhaging wound, including the steps of: using a transducer means, having an ultrasonic transducer having a transmitting surface emitting high frequency focused ultrasound having a frequency in the approximate range of 0.5 MHZ to 20 MHz and a depth of focus substantially immediately adjacent said transducer means, applying high intensity focused ultrasound energy onto outer regions of a hemorrhaging vessel adjacent to a puncture; and controlling energy level and the duration of exposure to cause closure of fibrous sheath tissue surrounding the puncture of the hemorrhaging vessel without substantially damaging wall tissue of the vessel itself.

In another basic aspect, the present invention provides a method for causing hemostasis of an internal hemorrhage, without surgical incision, by exposing a blood vessel or parenchyma source of the hemorrhage to sonic energy comprising high intensity focused ultrasound such that the hemorrhaging blood vessel or parenchyma is cauterized by the sonic energy.

In another basic aspect, the present invention provides a method of using high intensity focused ultrasound for surgical procedures, including the steps of: prior to incising tissue of a surgery patient, applying ultrasonic energy at a combination of frequency, time of exposure, and power intensity to cause controlled coagulation and necrotization of tissue in the patient such that a volume cauterized tissue region is formed in said tissue at predetermined locations within said tissue that are to be cut.

In another basic aspect, the present invention provides a high intensity focused ultrasound medical instrument. The instrument includes a pencil-like handle; fixedly mounted on a tip of the handle, a sealed acoustic coupling mechanism for interfacing ultrasonic energy into a patient; mounted subjacent the acoustic coupling mechanism, a ultrasound transducer mechanism, including at least one transducer for emitting ultrasonic energy through the acoustic coupling mechanism such that a focal region is produced immediately adjacent the acoustic coupling mechanism; and, incorporated through the handle, mechanisms for coupling the transducer mechanism to an electronic controller.

In another basic aspect, the present invention provides a high intensity focused ultrasound medical instrument including a palm-of-the-hand shaped and dimensioned handle; fixedly mounted on a first surface of the handle, a sealed acoustic coupling mechanism for interfacing ultrasonic energy into a patient; mounted on a second surface of the handle subjacent the acoustic coupling mechanism, an ultrasound transducer mechanism, including at least one transducer for emitting sonic energy through the acoustic coupling mechanism; and mounted on a third surface of the handle opposing the first surface, mechanisms for coupling the transducer mechanism to an electronic controller.

It is an advantage of the present invention that it provides a method for performing surgery while limiting hemorrhaging.

It is an advantage of the present invention that it provides a device for performing HIFU surgical procedures, particularly suited to performing percutaneous cauterization, hemostasis, and coagulative necrosis of tissue.

It is an advantage of the present invention that it provides a surgical device which can produce hemostasis along a defined focal path without deep penetration into tissues, without substantial charring of a cut tissue interface, and without harmful cavitation-related tissue damage.

It is another advantage of the present invention that it provides a method and apparatus for medical situations where conventional hemostatic mechanisms are either too slow or not functioning properly due to blood platelet or coagulation factor deficiencies.

It is another advantage of the present invention that it provides a method and apparatus that can substantially shorten the time of surgery, thereby reducing costs.

It is another advantage of the present invention that it provides a method and apparatus that decrease both the risk of bleeding and the need for transfusions.

It is still another advantage of the present invention that it provides a method and apparatus for reducing the morbidity and death associated with surgical procedures in which hemorrhaging is a frequent problem.

It is yet another advantage of the present invention that it allows the use of HIFU for medical procedures with the ability to focus and localize HIFU effects without effecting intervening or subjacent tissue and organs.

It is still another advantage of the present invention that it provides for a device that can be adapted to either open or laparoscopic surgical procedures.

It is a further advantage of the present invention that it provides a device for performing percutaneous embolization and partial resection operations, eliminating the need for organ removal.

It is yet a further advantage of the present invention that it provides a device suited for emergency surgical procedures for stemming bleeding due to vascular breaches.

It is a further advantage of the present invention that it provides a device for non-invasively stemming internal hemorrhaging.

It is still a further advantage of the present invention that it can be used in an emergency medical situation to decrease the effects of traumatic injury while the injured is transported to a fully equipped medical facility.

Other objects, features and advantages of the present invention will become apparent upon consideration of the following explanation and the accompanying drawings, in which like reference designations represent like features throughout the drawings.

BRIEF DESCRIPTION OF THE DRAWINGS

FIGS. 1A and 1B are schematic depictions of a presurgical medical procedure methodology in accordance with the present invention in which:

FIG. 1A is a top view of a section of a body organ having a tumor, and

FIG. 1B is a side view of the depiction of FIG. 1A in which presurgical volume cauterization has been performed.

FIGS. 2A through 2D are schematic depictions of various steps of the procedure as shown in FIGS. 1A–1B in which:

FIG. 2A depicts a first step involved in producing a vertical coagulated and necrotized line or plane, FIG. 2B depicts a second step involved in producing a vertical coagulated and necrotized line or plane, FIG. 2C depicts a third step involved in producing a vertical coagulated and necrotized line or plane, and FIG. 2D depicts a final step involved in producing a vertical coagulated and necrotized line or plane.

FIGS. 3A through 3F are perspective views depicting steps in the procedure as shown in FIGS. 1A–2D in which:

FIG. 3A depicts bottom burn paths using an apparatus as depicted in FIGS. 1A–2D, FIG. 3B is a subsequent step depicting a completed bottom burn as shown in FIG. 3A, FIG. 3C is a subsequent step depicting side burn paths, FIG. 3D is a subsequent step depicting a partially complete cauterization shell, FIG. 3E depicts a subsequent step depicting further side burn paths, and FIG. 3F depicts a subsequent step depicting a completed bottom and side plane cauterization shell.

FIGS. 4A through 4C are schematic drawings of an apparatus in accordance with the present invention for performing the procedures depicted in FIGS. 1A–3F in which:

FIG. 4A is a top view of the apparatus,

FIG. 4B is a side view of the apparatus,

FIG. 4C is a perspective view, schematic drawing of the mechanism of element 401 of FIGS. 4A and 4B.

FIGS. 5A through 5C are schematic diagrams in cross section (side view) showing an alternative embodiment of the apparatus as shown in FIGS. 4A–4C in which:

FIG. 5A is a top view of the apparatus,

FIG. 5B is a side view of the apparatus, and

FIG. 5C is a schematic drawing of the inner mechanism of element 501 of FIGS. 5A and 5B.

FIGS. 6A through 6C are schematic diagrams showing an alternative embodiment of the apparatus of the present invention depicting a side focusing unit in which:

FIG. 6A shows the unit projecting a depth of focus of a first depth,

FIG. 6B shows the unit projecting a depth of focus of a second depth, and

FIG. 6C shows the unit projecting a depth of focus of a third depth.

FIGS. 8A through 8E are schematic diagrams showing another alternative embodiment of the apparatus of the present invention depicting a hand-held unit, in which:

FIG. 8A shows a top view of the unit,

FIG. 8B shows a bottom view of the unit,

FIG. 8C shows the unit being used within a body cavity,

FIG. 8D shows an alternative set of transducers for the unit as shown in FIG. 8B, and FIG. 8E shows the embodiment of FIG. 8D in use.

FIGS. 13A and 13B are schematic drawings in cross section (elevation) of a telescoping embodiment of a device in accordance with the present invention in which:

FIG. 13A depicts the device in a fully retracted position, and

FIG. 13B depicts the device in an extended position.

FIGS. 15A through 15C are an alternative transducer mount and telescoping device for the embodiment as shown in FIGS. 13A and 13B in which:

FIG. 15A is an elevation view,

FIG. 15B is a perspective view, and

FIG. 15C is a perspective view in which part of the device has been removed.

Figure 3A:
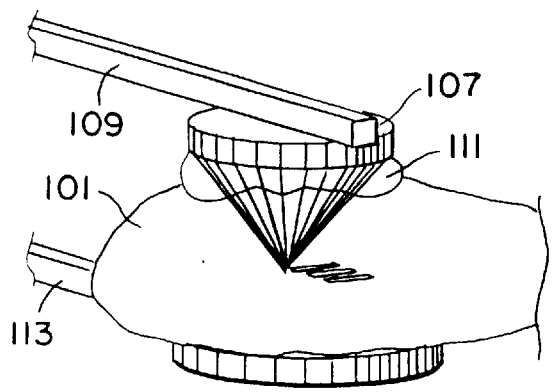

The drawings referred to in this specification should be understood as not being drawn to scale except if specifically noted.

DESCRIPTION OF THE PREFERRED EMBODIMENT

Reference is made now in detail to a specific embodiment of the present invention, which illustrates the best mode presently contemplated by the inventors for practicing the invention. Alternative embodiments are also briefly described as applicable. In order to describe the various aspects of the present invention and as several apparatus embodiments are disclosed, the methodologies of use are presented first. Subtitles provided herein are for convenience of the reader only and are not intended to define, describe, or place any limitation on the scope of the invention; no such intent nor limitation should be implied therefrom.

Presurgical Procedures

As set forth in the Background section, ultrasonic energy can be focused to produce hemo-coagulation and necrosis in living tissue. In FIG. 1A, there is shown a section of a liver 101, having a tumor 103. While such tumors are operable, because of the highly vascularized nature of the livers pathological constitution (the average blood flow is about 25% of the resting cardiac output and the liver is a relatively soft organ that tears easily), liver surgery places the patient at high risk, making the arresting of rapid liver hemorrhage or even slow oozing of blood with conventional methods a time-consuming and difficult task.

Looking also to FIG. 1B, a simplistically depicted, high-intensity focused ultrasound ("HIFU" hereinafter) apparatus 105, including an ultrasound transducer device 107 supported by a top arm 109 is brought into contact with the liver 101 by an acoustic coupler 111 used to couple acoustic energy to the liver tissue. The coupler 111 contains an acoustic-transmissive medium inside a flexible membrane. The membrane is highly elastic to conform to the anatomy, able to withstand the high ultrasonic intensities near the acoustic focus, sufficiently tough to survive in the surgical environment, and bio-compatible. It has been found that a polyether polyurethane provides a preferred material. The material is available commercially as PT9300 Dureflex™ polyurethane film, medical grade, 50 microns (0.002 inches) thick, made by Deerfield Urethane, South Deerfield, Mass. For certain of the coupling methods, e.g., water-filled cones as described herein, the elasticity requirements are relaxed, and it may be possible to use other types of plastic films.

A bottom arm 113 slips under the tissue and aids in fixing the distance between the transducer device 107 and the tumor 103. The transducer device 107 is then activated and used to describe a shell 115 of coagulated and necrotized tissue around the tumor 103. In other words, prior to any surgical incision, the tumor is encapsulated by a shell 115 of tissue that has been thoroughly cauterized using HIFU energy. The procedure for producing the shell 115 is referred to as "presurgical volume cauterization," the shell 115 comprising a volume of tissue equal to the surface area times the thickness of the shell.

Changes in the appearance of the cauterized planes 117, 119, and the like, of the shell 115 are highly visible after the volume cauterization process. The tissue is essentially "cooked;" that is, it hardens and is warm to the touch. The shell 115 then provides a coagulated surgical pathway. That is, surgical incisions are made along the coagulated pathway and little to no bleeding results. Note that while in this exemplary embodiment a box shaped shell 115 has been formed in the liver tissue, depending upon the surgery to be performed, virtually any shape necrosed surface can be formed as needed, e.g., flat planar, curved surface, open or closed cubes and rectangles, inverted wedge shapes, inverted pyramids, open or closed cylinders, or the like as would provide appropriate necrosed surgical pathways for the following operation. The goal is to isolate a region of tissue from the blood supply to it by surrounding the surgical target with a necrosed surface. The particular surface chosen is selected to minimize the removal of viable non-diseased tissue as well as to make it a practical resection procedure for the surgeon.

FIGS. 2A–2D depict specific steps of forming a vertical coagulated and necrotized line or plane during the volume cauterization process in further detail. In FIG. 2A, the transducer 107 provides a focal region 201 with a dimensional shape having a depth of field "a" at a depth of focus "b". The aperture dimensions, frequency, and physics of ultrasound energy propagation dictate the focal zone 201 dimensions. Note that the FIGURES are not intended to be to scale; in typical practice, it has been found that in preferred embodiments the length of the focal region can be about ten times its lateral width in order to optimize HIFU effects at the target. Tissue lesions generated by the HIFU beam are similar in shape to the focal region, but slightly broader nearer the transducer.

Appropriate continuous wave or pulsed acoustic energy (represented by phantom lines) is applied for a predetermined time (as also will be discussed in detail hereinafter) to necrotize the tissue of the exemplary liver 101. The depth of focus is then changed sequentially as depicted in FIGS. 2B–2D, producing a vertical coagulated and necrosed line, or plane, 203, FIG. 2D.

Figure 3B:
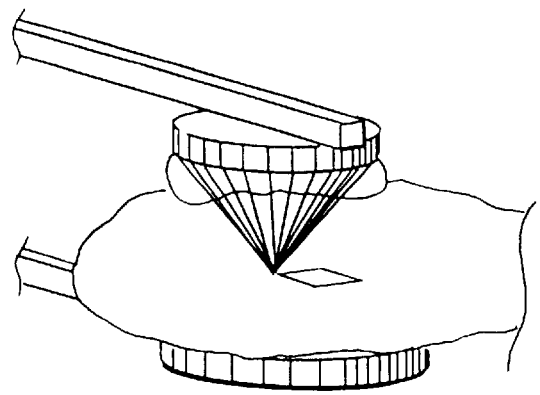
Figure 3C:
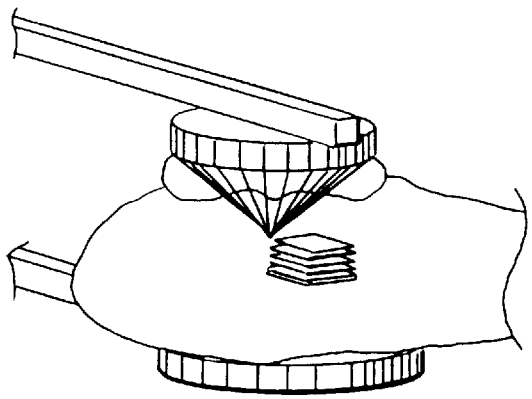
Figure 3D:
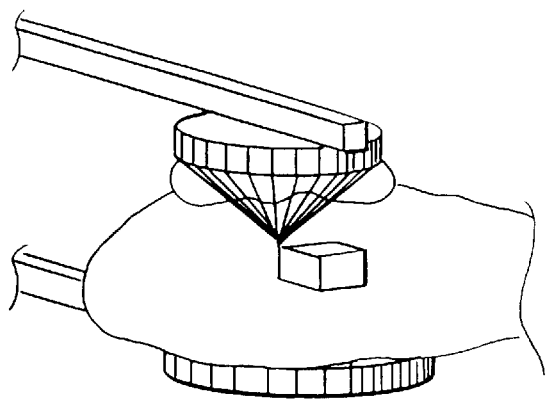
Figure 3E:
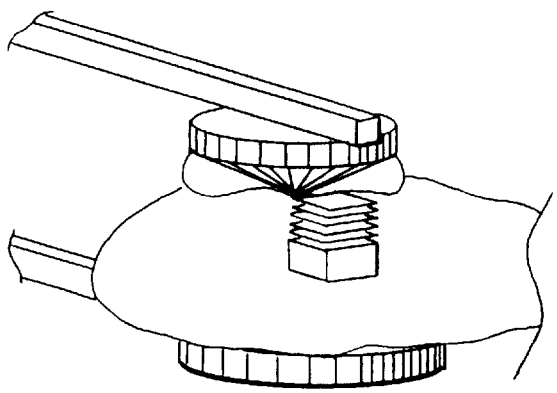
Figure 3F:
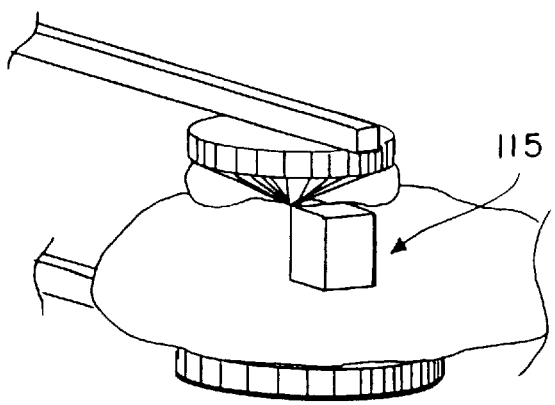

The concept of how the position of the focal point of the transducer can be varied to scan and produce a volume cauterization is shown in three dimension in FIGS. 3A–3F. FIG. 3A represents a transducer 107 focusing acoustic energy into a tissue mass 101 through an acoustic coupler 111. The transducer is being moved laterally in FIGS. 3A and 3B in order for form a burn path in the tissue approximating a planar surface, such as by cauterizing rows of adjacent tissue burns. In FIG. 3B, the entire planar surface is shown which actually forms a contiguous necrotized tissue volume having a small thickness equal to the depth of field of the particular transducer 107 in use. This contiguous necrotized tissue volume might be, for example, a plane beneath a tumor to be removed surgically. In FIG. 3C, the transducer is moved laterally to scribe a line defining the perimeter of a complete shell region to be cauterized, then moved vertically to scribe the next superjacent perimeter, et seq. as depicted in FIGS. 3D through 3F. In FIG. 3F, a complete open cubic volume shell has been formed. The shell so produced provides a surgical pathway where the surgeon may cut through the tissue with substantially no resultant bleeding.

It should be noted that in addition to the hyperthermia effects some cavitation effects may be present in tissue so treated in accordance with the foregoing procedures. The operative effect may thus be a combination of hyperthermia and cavitation; thus, further study is warranted.

HIFU Apparatus

A first embodiment of an apparatus 105 for performing presurgical volume cauterization as shown in FIGS. 2A through 3F is shown in FIGS. 4A–4E. Again, the liver 101 is used as an exemplary organ on which an invasive surgical procedure is to be performed. A bottom arm 113 is provided for resting under the tissue of the organ to aid in fixing the distance between the transducer device 107 and the focal points within the organ.

Note also that the bottom arm 113 can carry an acoustic absorber on the distal side of the tissue from where the ultrasound energy is applied. The general purpose is to absorb the ultrasound energy that passes through the tissue beyond the focal point, thereby insulating subjacent tissues from being insonified. One characteristic of such an absorber is that acoustic impedance (density times the speed of sound) should be ideally equal to the tissue. With such a characteristic most of the energy is absorbed and there is little reflection of the impinging energy back into the tissue. A second beneficial characteristic is to have the absorber have good acoustic absorbing properties at the frequency of the transducer emission, allowing acoustic energy to be absorbed rapidly. A third beneficial characteristic is to have the absorber material have a thickness and thermal properties such that the surface abutting the tissue does not become hot enough to affect it.

Tan gum rubber has a lower impedance, approximately 1.5 Mrayls, but its loss is only about 4.3 dB/cm at 1.0 MHZ. This is the best material known to date and, though requiring a thicker layer, such aids in distributing heat caused by energy absorbed and thus avoids developing a hot surface. An alternative is neoprene, commercially available (e.g., Gardico Inc., 1107 Elliott W., Seattle, Wash.), which has an impedance of 2.4 Mrayls, which results in only about a five percent reflection. Red SBR rubber has similar loss characteristics, but a higher impedance. However, red SBR rubber is adverse to wetting and an air layer between the rubber and tissue will greatly increase the reflection coefficient. Hydrophobic materials should be wetted with alcohol before immersion to minimize such effects.

In an alternative embodiment, material placed on the bottom arm 113 could be acoustically reflective. If the coefficient of reflectivity is high enough, little impinging energy will be transmitted to tissue or organs beyond, thus the same goal as using an absorber is achieved. The reflected energy can be used to enhance the procedure in the tissue of interest. A suitable reflector should have a characteristic of having an acoustic impedance much different from the tissue, either lower (such as air or an airfilled material like Styrofoam™) or much higher (e.g., ceramics). For a low impedance reflector, a 180° phase reversal is produced at the point of reflection. This tends to cancel the effect of the impinging and reflected wave in the region proximate to the reflector. For a high impedance reflector, there is no phase reversal, so the impinging and reflected waves superimpose, producing an increased heating effect. Thus, a high impedance reflector should be immediately subjacent the target region. Furthermore, a mirror-reflection of a diverging beam impinging on the reflector is further diverging. Therefore, it is possible to obtain a broader area of effect in the region proximate the reflector surface. If the focal point is closer to the transducer than the reflector, it is possible by superimposition to produce effects with broader beams beyond the maximum depth of focus.

Figure 4A:
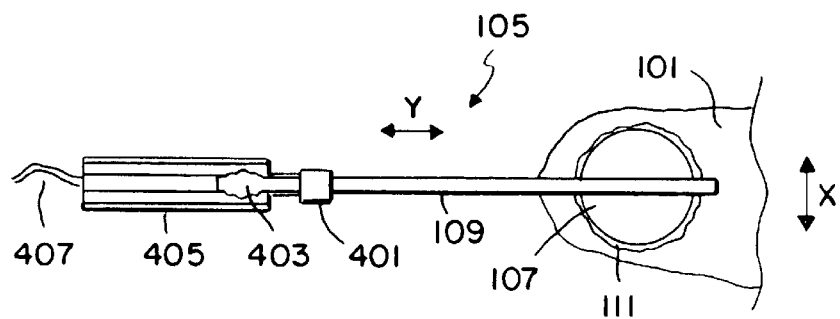
Figure 4B:
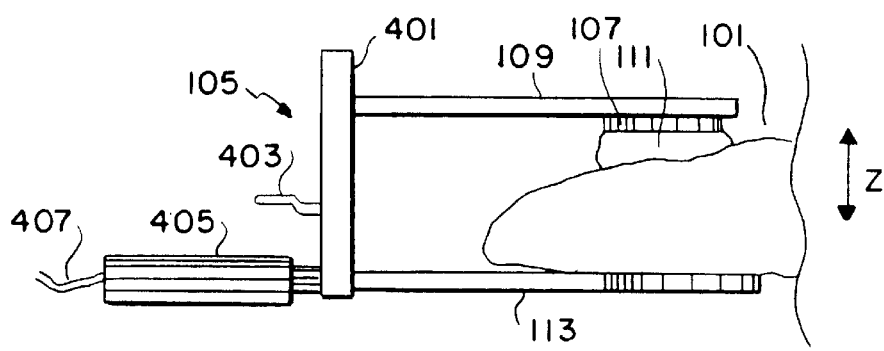

The transducer 107 and its acoustic coupler 111—in this embodiment a simple flexible cuff filled with water—are connected to a transducer aligning mechanism 401 by a top arm 109. The transducer aligning mechanism 401 is provided with a thumb trigger 403 adjacent an apparatus handle 405. The transducer aligning mechanism 401 detail is shown in FIG. 4C. The top arm 113 also bears electrical cabling 407 connected to an electronic controller (not shown, but see FIGS. 10–12).

Figure 4E:
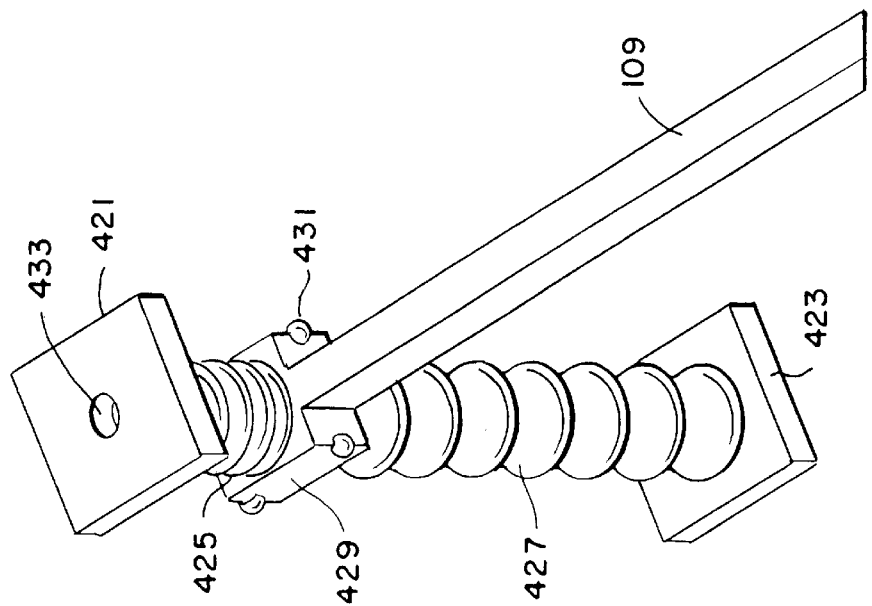
FIG. 4E is a perspective view, schematic drawing showing detail of the dynamic operating mechanism of element 401 of FIGS. 4A–4C.
Figure 4C:
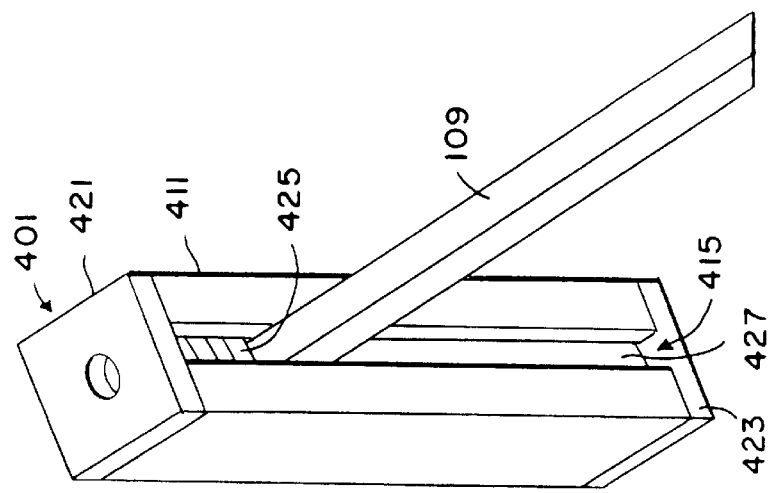
Figure 4D:
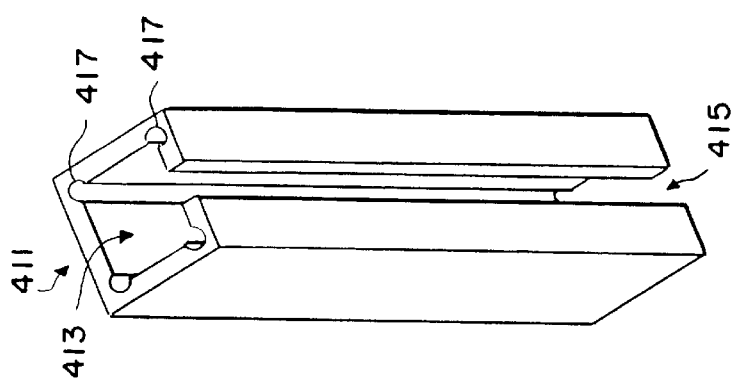
FIG. 4D is a perspective view, schematic drawing showing detail of element 411 of FIG. 4C.

Turning to FIGS. 4C–4E, the transducer aligning mechanism 401 provides one degree of motion in the Z-axis (FIG. 4B) to lower or elevate the transducer 107 with respect to the tissue, which essentially is used to change the depth of focus. The aligning mechanism 401 has a casing 411 having a hollow through channel 413 (FIG. 4D) and a slide channel 415 (FIGS. 4C and 4D). Arm 109 (FIGS. 4A, 4B, 4C and 4E) fits through the slide channel 415 to have freedom of motion in the Z-axis. Four ball bearing channels 417 (FIG. 4D) are provided in each interior corner of the casing 411.

An upper end cap 421 and lower end cap 423 close the through channel 413 of casing 411 at each end. As shown in FIG. 4D and 4E, the arm 109 is mounted between an upper bellows 425 and a lower bellows 427 contained within the through channel 413 by a mount 429 at an end distally located from the transducer 107 (FIGS. 4A and 4B). The bellows-arm mount 429 has a size and exterior shape conforming to through channel 413 for a sliding fit therein. A ball bearing 431 mounted for rotation in cavities in each corner of the bellows-arm mount 429 to fit in respective ball bearing channels 417 of the casing 411 so that the mount rides freely in the Z-axis. The end caps 421, 423 are provided with bellows pressurizing apertures 433 (lower cap aperture not shown) for connecting a suitable pressurizing/depressurizing medium, e.g., an air supply and tubing (not shown), to each bellows 425, 427. The thumb trigger 403 (FIGS. 4A & 4B) is coupled to the air supply and used to pneumatically control Z-axis motion of the arm 109 via the bellows 425, 427. Selectively increasing the pressure in one bellows while decreasing the pressure in the other allows the bellows to expand and contract respectively, causing the arm 109 to move in the slide channel 415 and directly translated to the transducer 107. The rate of flow of pressurized air is set at the pressure source to a limited value to control the speed that the bellows inflate-deflate, controlling the speed that the arm 109 is raised or lowered.

Motion in directions other than the Z-axis are done manually. That is, using the handle 405, the surgeon slides the apparatus 105 towards or away from himself or laterally across the surface of the organ 101 to move the focal point in a line. If the transducer is of a semi-cylindrical configuration that is forming a line of coagulated and necrosed tissue (see FIG. 9 described hereinafter), moving the apparatus 105 towards or away from himself describes a horizontal plane; moving the apparatus in the Z-axis then describes a vertical plane. Thus, as can now be recognized by a person skilled in the art, a variety of transducer configurations, described hereinafter, and relative motion will produce a variety of shapes and sizes of volume cauterization regions.

Figure 5A:
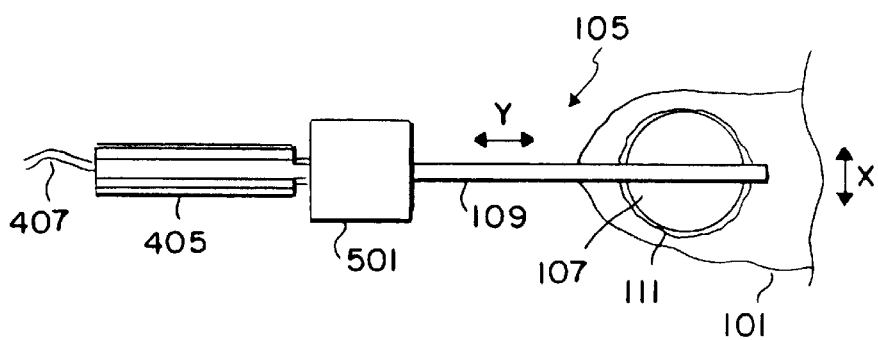
Figure 5B:
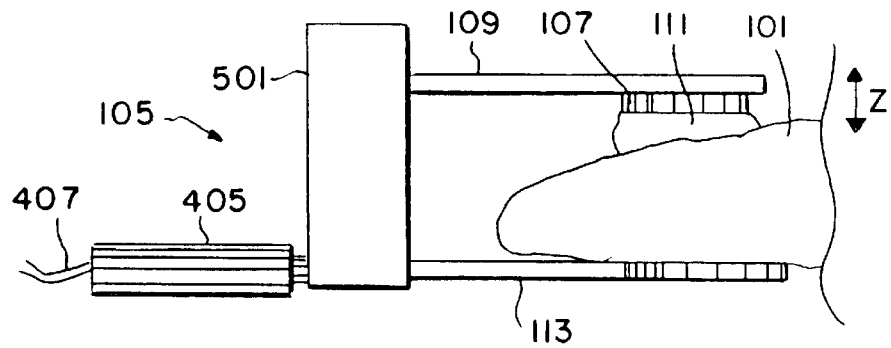
Figure 5C:
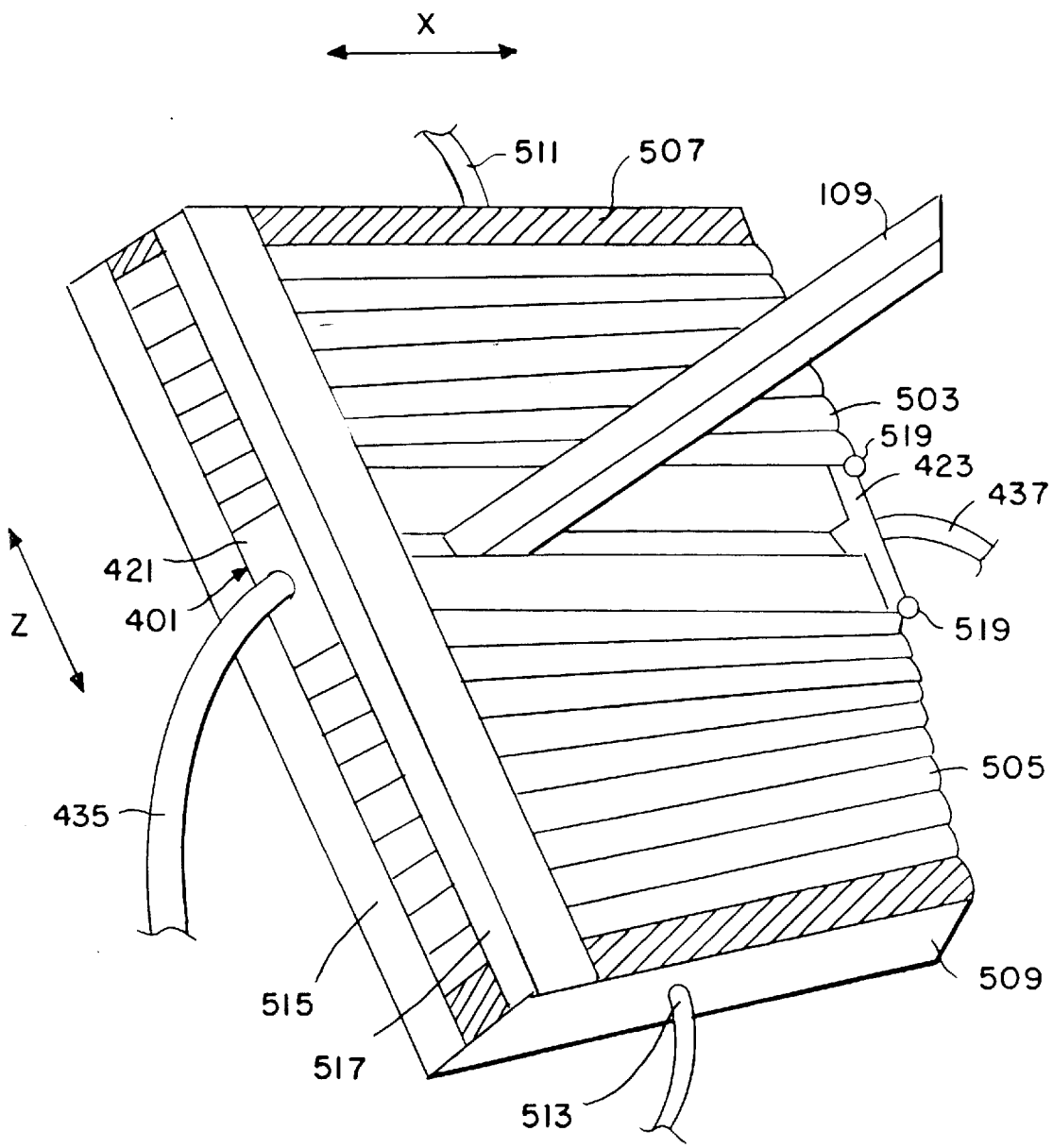

An advanced embodiment is shown in FIGS. 5A–5C in which the transducer aligning mechanism 401 of FIGS. 4A–4C has been replaced with an electro-mechanically controlled transducer positioning assembly for moving the top arm 109, or top and bottom arms 109, 113, in the X-, and Z-axes. Turning to FIG. 5C for details of the transducer positioning assembly 501, the mechanism 401 (FIG. 4C) has been modified to add the additional degree of motion control. The arm 109 is moved in the X-axis by turning the transducer aligning mechanism 401 to a horizontal orientation. Two pneumatic bellows 503, 505 are linked together to produce the Zaxis motion. A top bellows cap 507 and bottom bellows cap 509 are provided with apertures for receiving air supply tubes 511, 513 in the same manner as the caps 421, 423 of the transducer aligning mechanism 401, now shown as tubes 435, 437. Left bellows corner struts 515, 517 and right bellows corner struts (not shown) are used as guides for ball bearings 519 captured in the external corners of transducer aligning mechanism end caps 421, 423 for mating with the struts such that inflating and deflating the top bellows 503 and bottom bellows 505 causes controlled motion in the Z-axis. Thus, the four corner struts hold the assembly rigid and allow the X-axis mechanism 401 to move up and down using the external pneumatic controller (not shown).

In another embodiment, not shown, a third pair of bellows can be added to the assembly of FIG. 5C to provide y-axis control (FIG. 5A). The operator's control can be a joy-stick, foot controls, or the like, as would be known in the art.

Figure 6A:
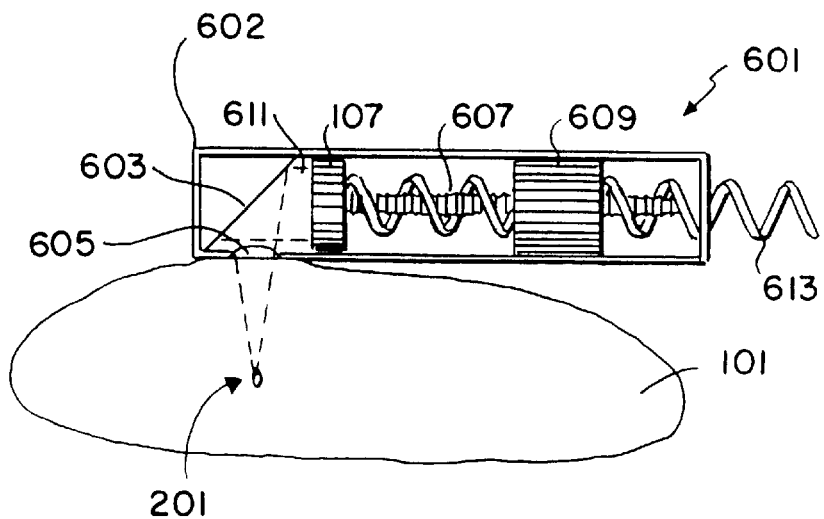
Figure 6B:
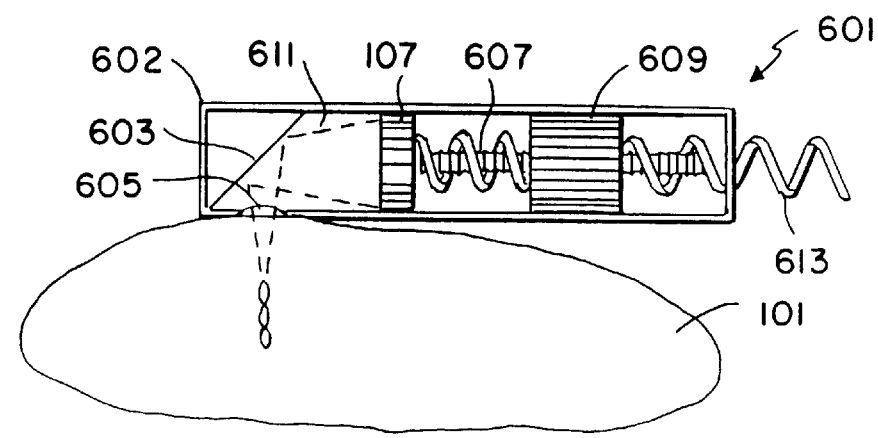
Figure 6C:
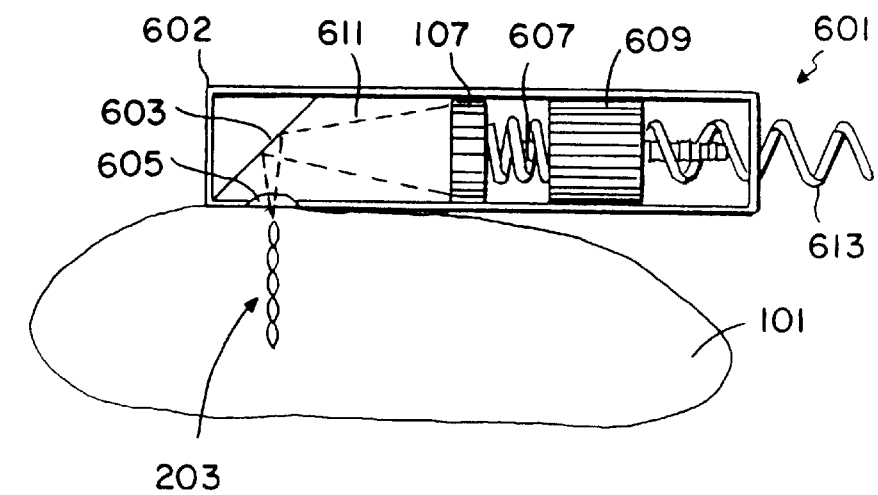

Depth of focus can be more easily accomplished by an alternate embodiment as shown in FIGS. 6A–6C. A side-radiating HIFU unit 601, having a housing which doubles as a handle, 602 uses an acoustic energy reflector 603 to focus ultrasonic energy, represented by the phantom lines, transmitted through a suitable fluid medium 611, out through an acoustic energy window 605 into the organ 101. The HIFU reflector 603 is at an angle of approximately 45° to the handle 602 orientation, bending the ultrasound beam 90°. The depth of focus is varied using a drive screw 607 powered by a motor, or other linear drive mechanism, 609 to change the distance between the emitter face of the transducer 107 and the acoustic energy reflector 603. Electrical energy for the motor 609 and transducer 107 is provided using a flexible cable 613. FIGS. 6A–6C again illustrate how a line or plane of coagulation can be produced by moving the position of the transducer with respect to the reflector. In a further refinement, the reflector 603 can be oscillated about its center line to sweep a point focus precisely in a plane perpendicular to the axis of the handle 602.

Figure 7:
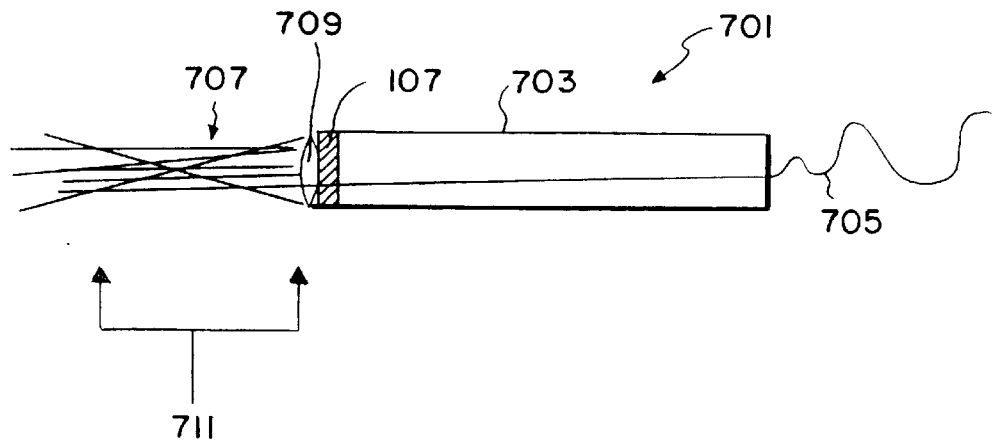
FIG. 7 is a schematic diagram showing an alternative embodiment of the apparatus of the present invention presenting a front focusing unit.

FIG. 7 demonstrates an even further simplified HIFU tool 701 in the nature of a pencil-like probe 703. The probe 703 has a transducer 107 with an appropriate electrical connection 705. Acoustic energy 707 is transmitted through a fluid coupling window 709. The combination of an essentially zero depth of field characteristic with a short, fixed, focal length 711 provides for cauterizing tissue immediately in front of the window 709 to the extent of the depth of field of the transducer 107. Thus, a surgeon could cauterize a line of tissue, cut the line with a scalpel, then reapply the probe 703 to cauterize a next line of tissue to be cut—viz., cauterize, cut, cauterize, cut, etc.—as needed step by step in the operation. Such an embodiment would be more useful in a more general exploratory surgery or emergency surgical situations where an exact surgical target location is undefined.

Figure 8A:
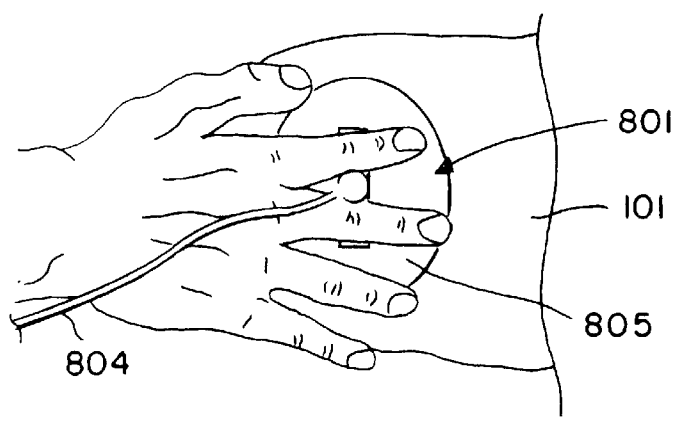
Figure 8B:
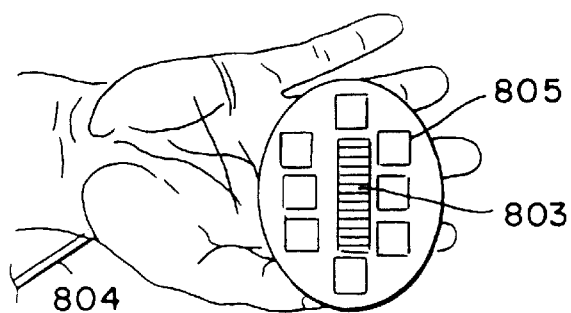
Figure 8C:
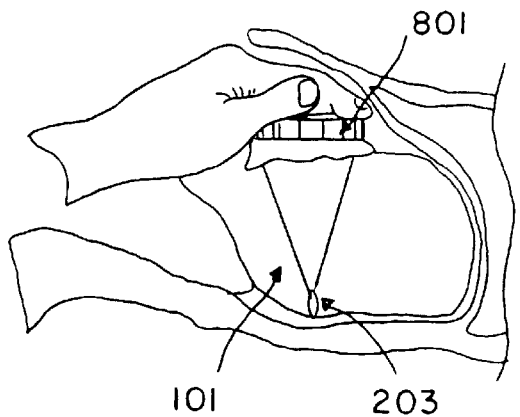

Ultrasound is strongly reflected by air and bone interfaces. Thus, the application of HIFU surgery must be limited to those soft tissues in which a target region is identified. Intervening bones and air, viz., in the lungs, must be moved aside. FIGS. 8A–8C demonstrate yet another embodiment which is a hand-held HIFU surgical instrument 801, especially suited to emergency situation use or use within a region of the body cavity where it may be difficult to reach or see with more complex instruments such as shown in FIGS. 1A through 6C.

The imaging transducer 803 is a linear array used for steering as would be known in the art. An imaging device, such as a central linear transducer array 803, connected via cabling 804 to appropriate imaging equipment as would be known in the art, aids the surgeon in determining where to produce the HIFU cauterization effects. As the user moves the instrument 801 around within the patient, they receive an image of the underlying organ to guide placement of the instrument 801 in order to align HIFU transducer array elements 805 of a cauterizing transducer array set. Such an array is advantageous in this embodiment since electronically controlled depth of focus control can be provided through phase alignment of the elements 805. The HIFU transducer is a group of square or rectangular elements 805 located around the imaging transducer 803. The array is used as the HIFU application transducer, allowing an electronically controlled change of the focal depth, depending on the phasing of excitation to each element 805. Thus, the instrument 801 can be steered to some extent as well as focused at different depths and beam diameters depending on the phasing of the excitation to each element 805.

Figure 8D:
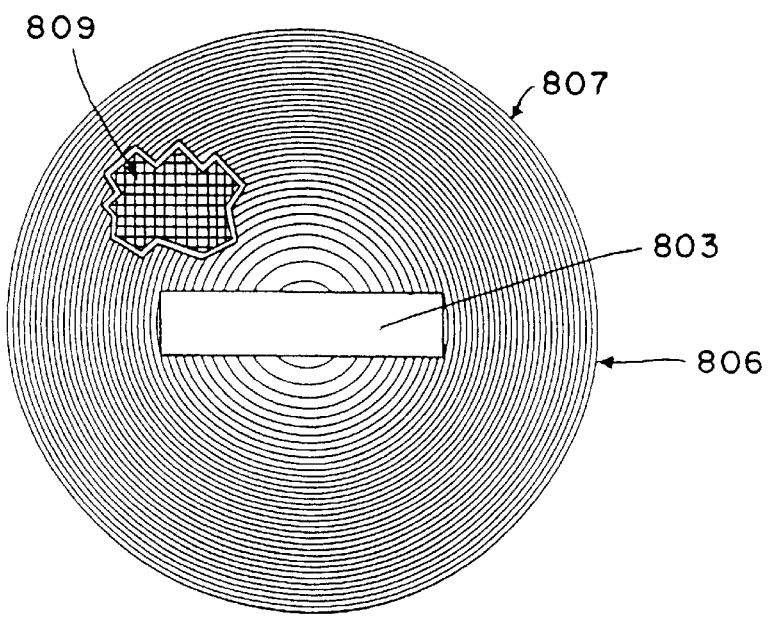
Figure 8E:
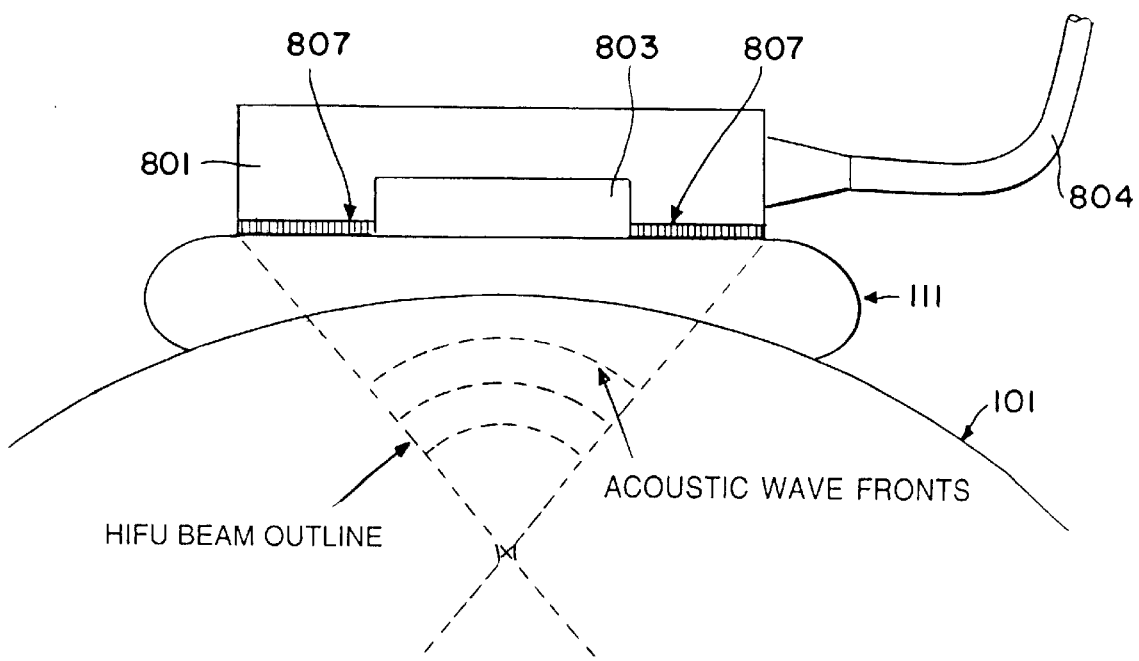

FIGS. 8D and 8E shows an alternative for the transducer arrangement using an annular array 806. [Some annular array instruments are known in the art. For example, in U.S. Pat. No. 5,520,188, Hennige et al., assignors to Focus Surgery, Inc., describe an annular array transducer for use in a localization and therapeutic ultrasound system where elements operate together to focus a continuous wave (CW) ultrasound beam at a focal zone that is a variable distance from the elements, including a mechanism to adjust the focal distance via adjusting the phase of the signals imparted to each element. See also e.g., *Intracavity Ultrasound Phased Arrays for Noninvasive Prostate Surgery*, Hutchinson and Hynynen, *IEEE Transactions on Ultrasonics, Ferroelectrics, and Frequency Control*, November 1996, Vol. 43, No. 6 (ISSN 0885-3010), pages 1032–1042; *Ultrasound Surgery Companson of Strategies Using Phased Array Systems*, Hong Wan et al., on multiple focal length designs, id. at pages 1085–1098; and *Sparse Random Ultrasound Phased Array for Focal Surgery*, Goss et al., id., pages 1111–1121; and *Design of Focused Ultrasound Surgery Transducers*, Rivens et al., ibid. at pages 1023–1031, discussing a method for determination of transducer configurations for different fixed focal lengths.] The annular transducer elements 807 enable an adjustable focal depth having a wider range than other configurations. Cutaway region 809 shows a sectional view of dicing pitch of the transducer elements 807. Providing linear separation of the elements, in perpendicular axes, also allows beam steering without the requirement of complex X-, Y-, and Z-axis driving mechanisms as shown in FIGS. 4A through 5B and equivalents thereof.

Other Transducers

A variety of transducer designs as would be known to a person skill in the art can be made for use in accordance with the present invention. For example, current state of the art for focused bowl transducers is discussed by Rivens et al., Design of Focused Ultrasound Surgery Transducers, IEEE Transactions, supra. In commercial therapeutic treatment, Sonic Focus Inc., Fremont, Calif., manufactures a HIFU system, Sonablate-1™, providing a transrectal probe for prostate hyperthermia treatments.

Figure 9:
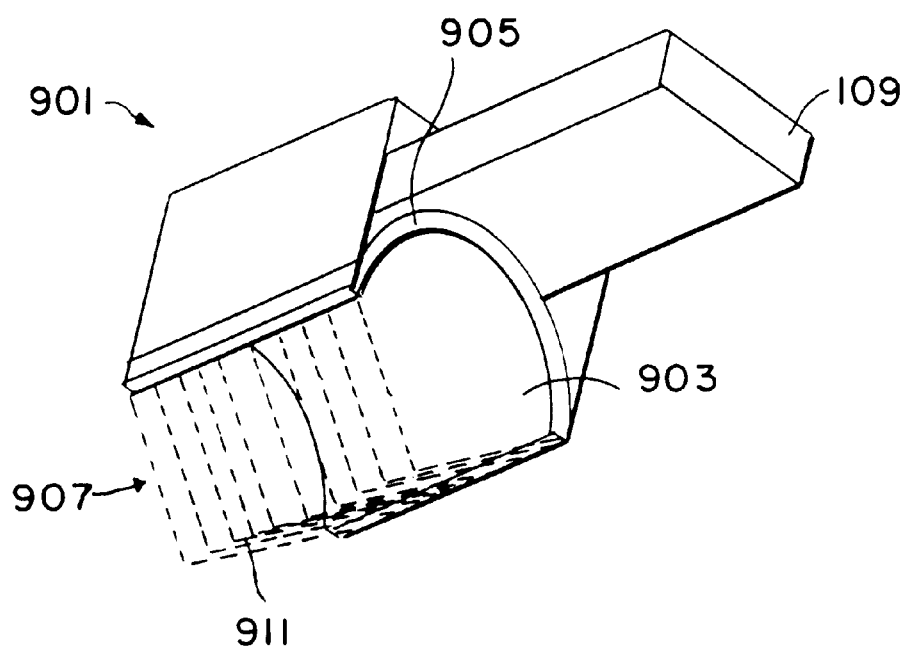
FIG. 9 is a perspective view, schematic drawing of a line focus transducer adaptable to use in accordance with the present invention such as shown in FIGS. 1B through 5B.

An exemplary embodiment for producing a focal line is shown in FIG. 9. The transducer 901 has an acoustic energy emitting surface 903 which is a portion of a cylinder 905. This cylindrical transducer 901 focuses ultrasonic energy (indicated by phantom lines 907) into a line 911. The distance of this focal line 911 from the transducer face 903 is approximately the radius of curvature of the cylindrical element 905.

Controllers

A variety of means for targeting acoustic transducers are well known in the art (see e.g., U.S. Pat. Nos. 4,484,569, 4,858,613, 5,520,188; Hynynen et al., Feasibility of Using Ultrasound Phased Arrays for MRI Monitored Noninvasive Surgery, and Thomas et al., Ultrasonic Beam Focusing Through Tissue Inhomogeneities with a Time Reversal Mirror: Application to Transskull Therapy, IEEE Transactions,. supra). Generally, a further description of specific target acquisition, such as finding a tumor within the liver, is not necessary to an understanding of the present invention.

Figure 10:
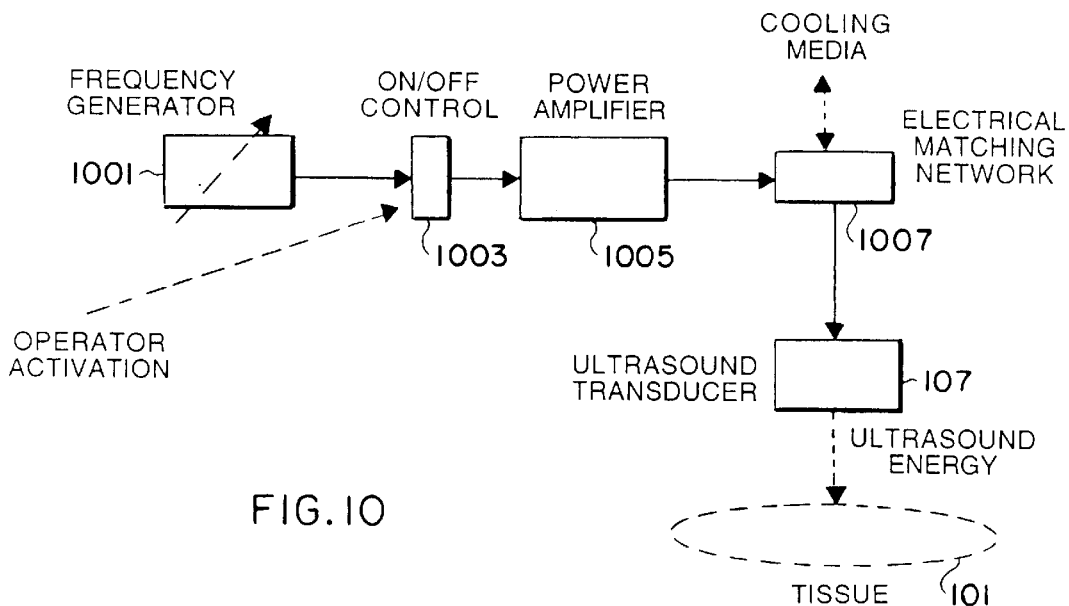
FIG. 10 is a block diagram of an electrical controller for a single channel system in accordance with the present invention.

FIG. 10 is a schematic diagram for a single channel controller embodiment of the present invention such as exemplified in FIGS. 6A–6C and 7. A frequency, or function, generator 1001 (such as a Hewlett-Packard™ Model 33120 Function Waveform Generator) is used to generate a waveform for exciting the transducer 107. The waveform signal is transmitted through an on/off switching control 1003 that is operator activated (see broken line arrow labeled "Operator Activation"); alternatively, preset timer activation can be provided. A power amplifier 1005 (e.g., an Electronic Navigation Industries™ Model API 400B) increases the generator 1001 output and sends it through an electrical matching network 1007 (having appropriate air or liquid cooling, if required) to the transducer 107. The matching network 1007 transforms the complex electrical input impedance of the transducer 107 into a nominally real impedance compatible with the output stage of the power amplifier 1005. As described above, the transducer 107 emits ultrasound energy in a pattern and intensity to produce tissue coagulation at particular intra-tissue sites. The frequency range useful in accordance with the present is approximates one-half (0.5) to twenty (20) MHZ. At higher frequencies, absorption is almost immediate, providing negligible penetration through living tissue It is intended that the frequency and amplitude are adjustable to suit a particular implementation or surgical need. The amplitude of the waveform signal at the output of the generator has enough amplitude, e.g., one volt RMS, so that the power amplifier 1005 will increase it to a magnitude whereby the transducer will have a sufficiently high enough output to produce tissue coagulation. For example, the electrical power being transmitted from the power amplifier 1005 may be in the region of 200 watts, which for a 50-ohm load would require 100 volts RMS output across the load. In turn the transducer 107 may then deliver intensity at a focal point of 1500 W/cm$^2$. It is believed that a spatial peak intensity in the range of 1300 to 3000 W/cm$^2$ may be applied to obtain appropriate results sought to be achieved present invention. Note carefully that intensity required to depends upon the chosen ultrasonic frequency and the frequency-dependent tissue attenuation rate. The values that are given may be appropriate in accordance with actual experimental studies that were performed at 1 to 3 MHZ (further details of which are not necessary to an understanding of the present invention). At higher frequencies (e.g., 5 to 10 MHZ) tissue attenuation will be proportionately higher, and the required focal intensity may be much lower. In terms of the desired thermal bioeffect, values can be converted to a specific absorption rate ("SAR") value, in units of Watts per kilogram. SAR values are commonly used in ultrasound hyperthermia studies and analysis. The SAR value specifies the amount of thermal energy that is being deposited per unit weight in the tissue, and it includes the effect of frequency-dependent attenuation. To achieve a certain temperature rise within a specified period, it may be more meaningful to use the SAR value. Equivalently, one could specify the ultrasonic intensity, the ultrasonic frequency, and the tissue attenuation rate.

While temperature elevation by ultrasound has been studied and reported upon (see e.g., Nyborg et al., Temperature Elevation in a Beam of Ultrasound, Ultrasound in Med. & Biol., Vol. 9, No. 6, pp. 611–620, 1983), in addition to specific transducer instrument operating parameters, various power, frequency, and time of application combinations are also dependent on a number of factors. For example, the type of tissue in which coagulation and necrotization is desired must be taken into consideration as different tissue will promote different absorption effects. Absorption of sonic energy are both frequency and tissue dependent. Another obvious variable is whether the HIFU energy is being applied in a pulsed or continuous wave form. Moreover, frequency independent data is an artifact of empirically competing effects of the absorption of sonic energy increasing with frequency and the size of the acoustic focal point depth of field decreasing with increased frequency. In other words, the energy intensity level, the sonic frequency employed, and the time of exposure, in either a pulsed or continuous wave modes, is primarily an empirical function. Each specific implementation may require empirically determined operational criteria.

If the ultrasonic frequency that is employed is too low, most of the energy will propagate past the depth of interest. Although this can be overcome by increasing the energy input, the energy that is deposited beyond the depth of interest is likely to damage tissues beyond the treatment zone. If an acoustic absorber is used, the waste energy will be converted to heat; this may protect deeper tissues, but significant heating may occur in the vicinity of the absorber.

Similarly, if the ultrasonic frequency that is employed is too high, most of the energy will be absorbed proximal to the depth of interest. Although this can be overcome by increasing the energy input, the energy that is deposited proximal to the depth of interest is likely to damage tissues.

In a homogeneous attenuative medium that behaves linearly with respect to pressure amplitude, it can be shown mathematically that for a plane wave, optimal energy deposition occurs at a depth "z" when the ultrasonic intensity at that depth is equal to:

$$I(z)=I_0/e \approx 0.368 * I_0,$$

where:

$I_0$=ultrasonic intensity at the surface of the attenuative region.

Figure 16:
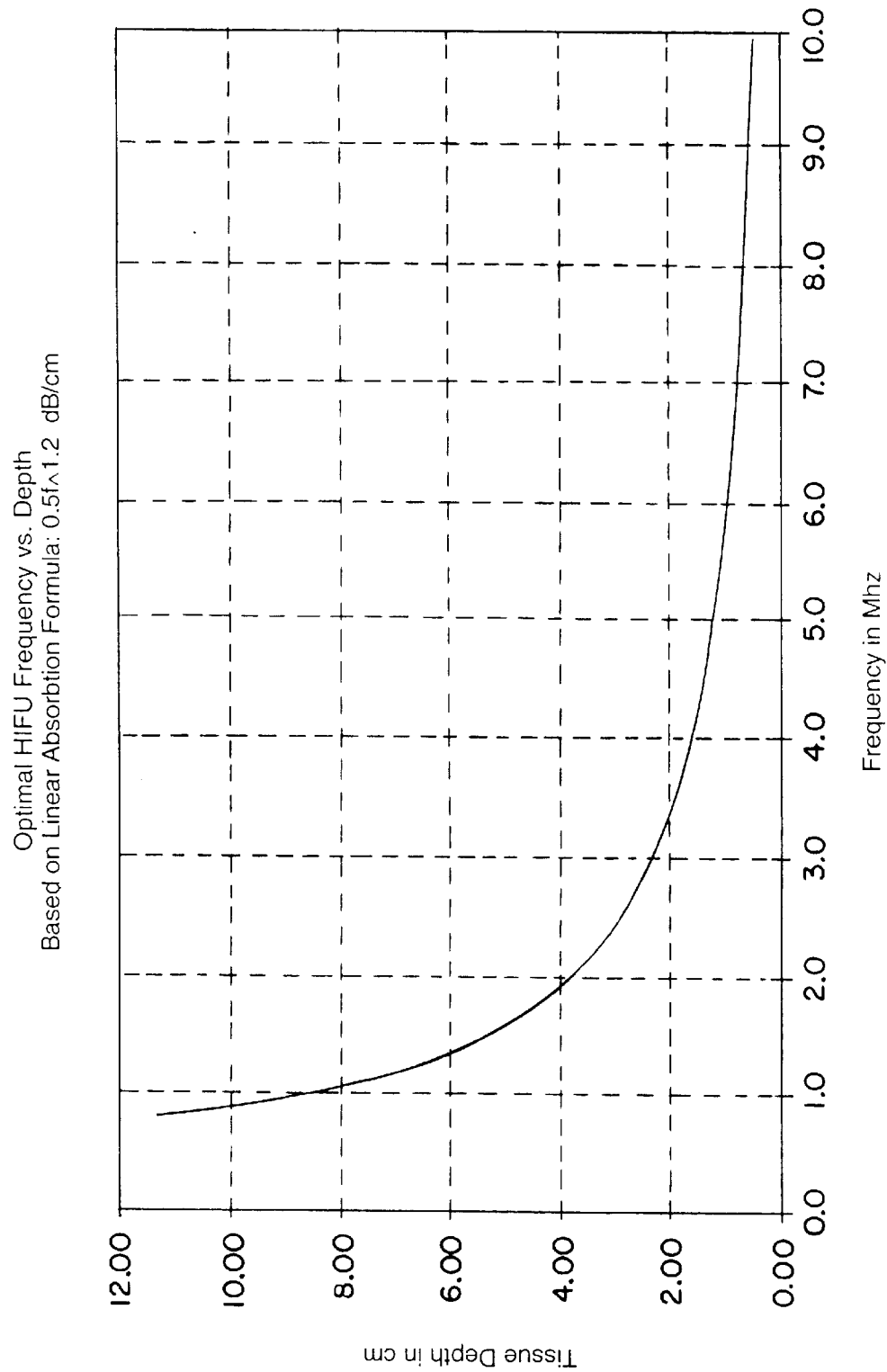
FIG. 16 is a graph showing an optimal HIFU Frequency vs. Tissue Depth plot.

The above formula maximizes the energy deposited at depth "Z" for a given amount of input power. Given the frequency dependence of the attenuation, one can calculate the optimal frequency to deposit energy at depth "z" (see attached graph of FIG. 16). Following this formula, note that only 37% of the input energy propagates beyond depth "z"; 63% is deposited between the surface and depth "z".

Focusing makes this argument more complex, but it does not alter the basic result. Weak focusing can be used to uniformly deposit energy from the surface to a depth "z" in a truncated conic zone; in this case, the beam cross-sectional area at depth "z" must be equal to:

$$A(z)=A_0/e \approx 0.368 * A_0,$$

where:

$A_0$=beam cross-sectional area at the surface of the attenuative region.

Thus, to produce high ultrasonic intensity at a depth "z", a focal intensity gain that is significantly greater than $e \approx 2.718$ is required.

In HIFU, attenuation is believed to be weakly non-linear with pressure amplitude in pre- and post-focal regions, and moderately non-linear near the focus. Nonetheless, the formulas above can be used to identify initial conditions. In practice, each specific clinical application will require some experimental optimization.

Note that optimal energy deposition requires a system and transducer capable of delivering energy at higher frequencies at shallow depths, and lower frequencies at deeper depths.

Figure 11:
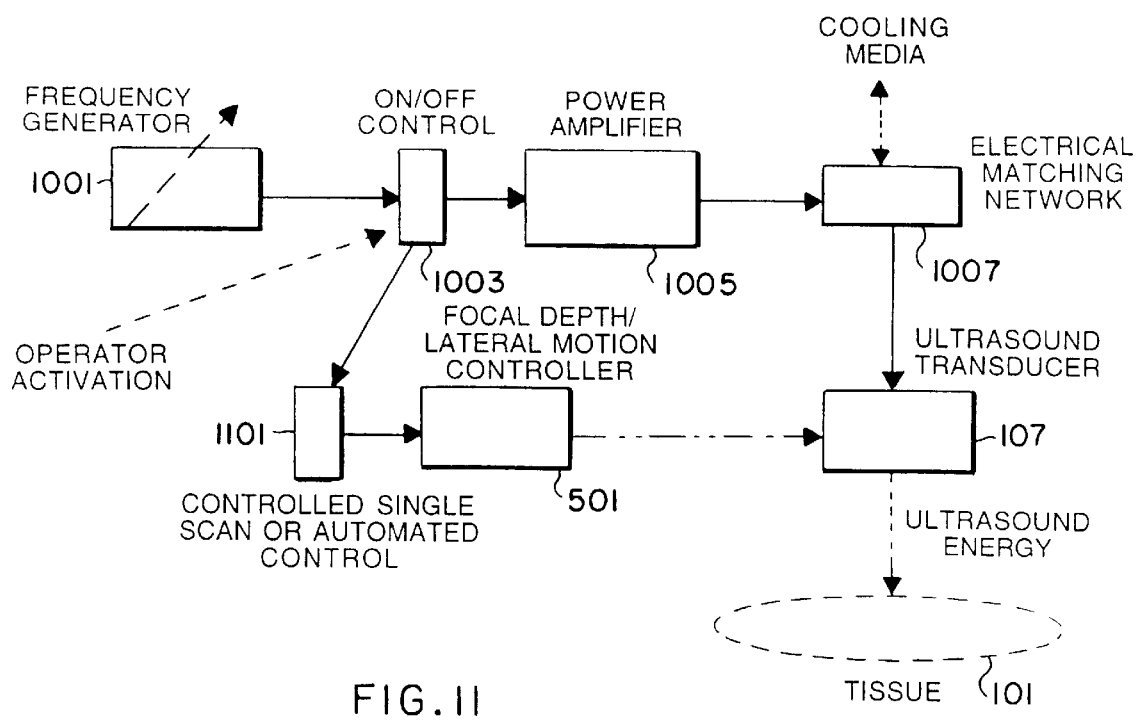
FIG. 11 is a block diagram of an electrical controller for a single channel system in accordance with the present invention having a focal depth controller as shown in FIGS. 5A–5B.

A second controller embodiment is shown in FIG. 11. Here the system is used to control the variation of the depth of focus for embodiments such as shown in FIGS. 4A–5B. In operation, activation of the on/off control 1003 causes the system to begin applying energy at a distal point in the tissue, moving it progressively closer to the transducer 107 with time. Under programmed control 1101, the circuitry automatically arms itself to position the transducer to perform a distal to proximal scan and then signals when ready. The operator turns on the apparatus and a scan is performed. After the scan, the transducer 107 is repositioned via transducer positioning assembly 501 to the next line or plane to be coagulated where a next scan is required.

Figure 12:
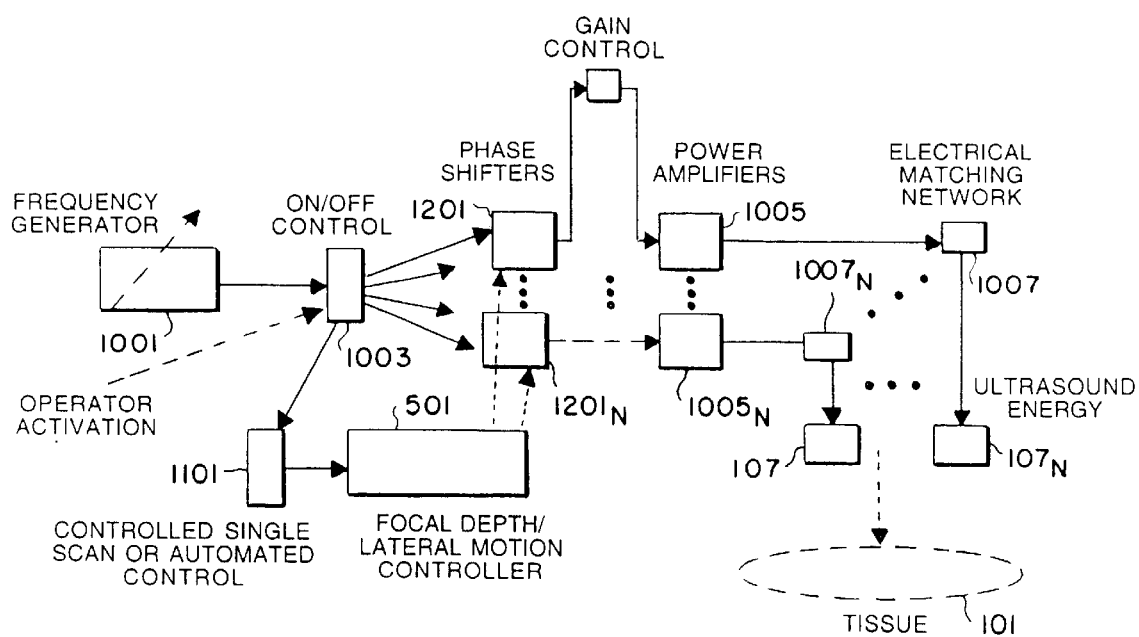
FIG. 12 is a block diagram of an electrical controller for a multi-channel system in accordance with the present invention as shown in FIG. 8B.

Shown in FIG. 12 is an electronic scanning system, useful with a phased array embodiment such as shown in FIG. 8B, or other electronically focused transducer. Added to the system are phase shifters $1201-1201_N$ in order to accommodate each transducer element $107-107_N$ in the annular array 805 (FIG. 8B). Programmed electronic depth of focus is provided as would be well known in the state of the art. Note that the controller can be adapted to provide a pulsed, continuous wave, or combination pulsed and continuous wave sonic energy emission from the transducer.

Independent control $1203_1-1203_n$ over amplitude and phase is provided. Independent amplitude control is necessary to produce desired apodization (shading) functions across the array aperture, which in turn results in control of side lobe levels. High side lobe levels may cause unwanted tissue damage in adjacent structures. These levels are easily reduced by the use of appropriate apodization functions. This is well known in the prior art. Independent channel gain controls would also be required if the transducer includes elements with unequal areas. In certain embodiments, e.g., an annular array with a central rectangular opening for an imaging array as depicted in FIG. 8D, the array elements will clearly have different elemental areas, requiring channel-independent gain.

Variable Depth of Focus Instrument Embodiments

As depicted in several drawing heretofore, a flexible bag 111 is provided as an acoustic coupler between the transducer 107 and the organic tissue 111. While adequate for certain uses, because of its inherent flaccid nature, there can be difficulty in maintaining both constant contact between the bag and the tissue and an accurate depth of focus.

Figure 13A:
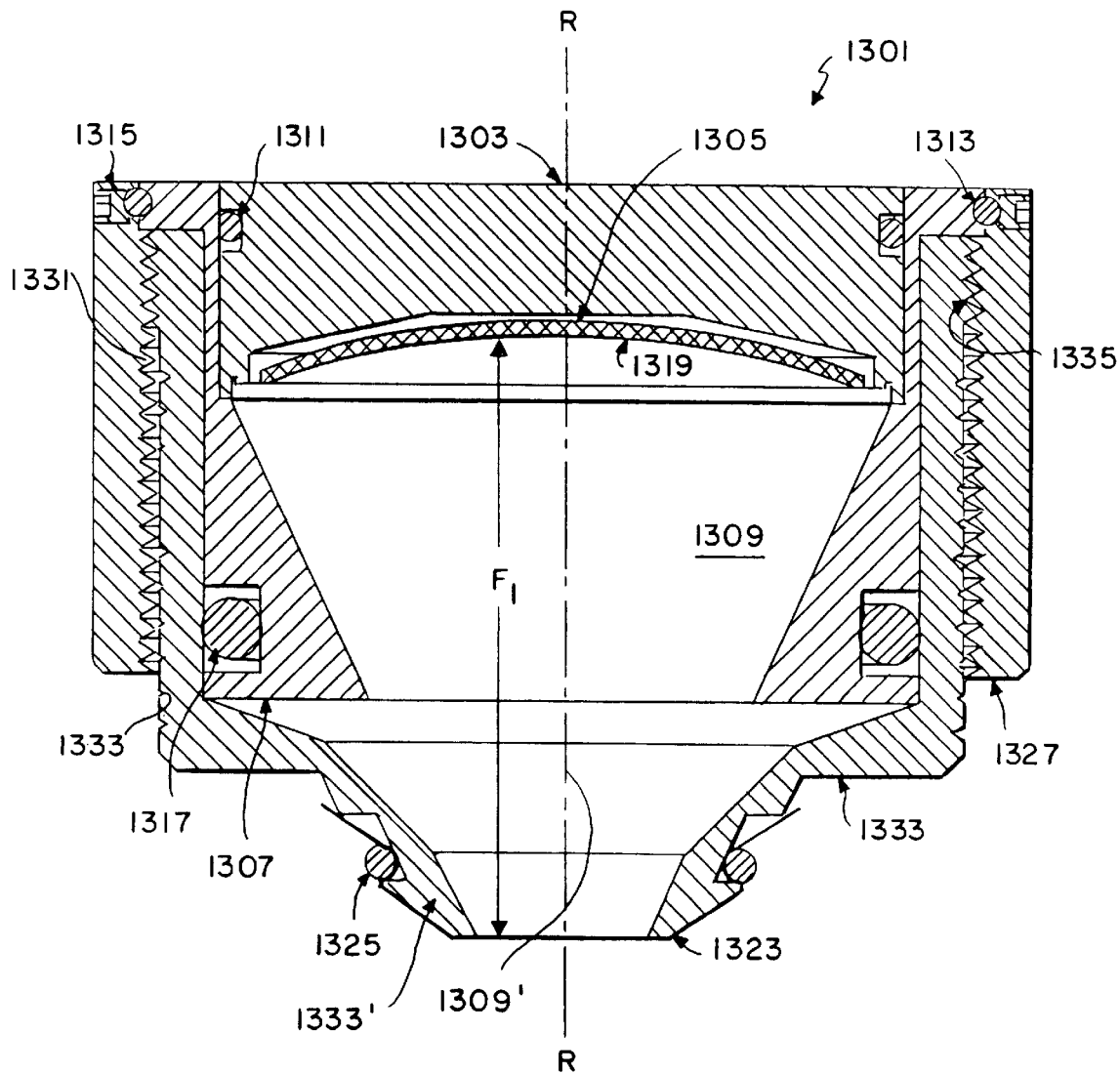
Figure 13B:
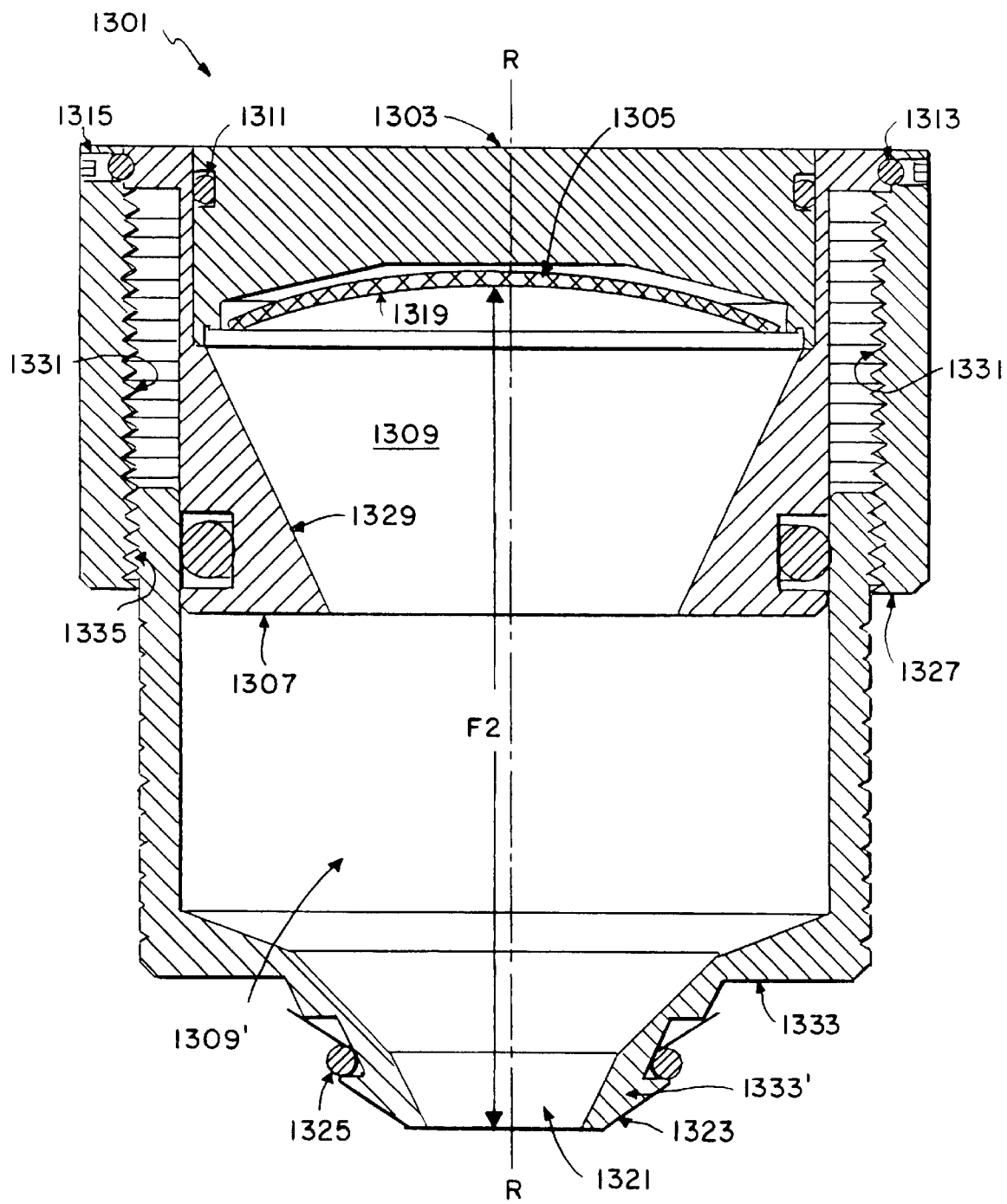

A HIFU tool assembly, having a true variable depth of focus in accordance with a preferred embodiment of the apparatus of the present invention is shown in FIGS. 13A and 13B. FIG. 13A depicts a presurgical device 1301 for preparing an organ of a patient for surgical incisions using HIFU energy to produce coagulation and necrosis in the tissue along each predetermined incision pathway, or using a very shallow depth of focus setting, for producing localized hemostasis (discussed in further detail hereinafter).

A transducer mount 1303 holds a transducer, or transducer array, 1305 in a substantially fixed configuration. A housing 1307, such as of a molded, clear, plexiglass, forms an internal chamber 1309. The device 1301 is mounted on a suitable handle, such as handle 109 of FIGS. 3A–4B, having inlet and outlet tubes (not shown; but see FIGS. 4A–5B, re element 407) allowing a suitable acoustic energy transmitting medium, such as water to flow into and out of the chamber 1309. The handle also carries any electrical wires or cables needed to power the transducer 1305. The housing 1307 has a rotatable collar 1327, having a fixed radial position relative to the transducer's energy emitting surface 1319 and an inner wall 1329 of the housing 1307. The housing inner wall 1329 at least partially forms the sides of the internal chamber 1309. The rotatable collar 1327 has screw threads 1331 on an interior surface thereof. A selectively movable focusing cone 1333 is coupled to the rotatable collar 1327 via focusing cone member screw threads 1335. When so mated, distally located from the transducer's energy emitting surface 1319, there is an acoustic window 1321 at a conical, lower extremity 1333' of the focusing cone 1333. An acoustically-transmissive, flexible membrane 1323 is stretched across the window 1321, secured to the housing 1307 by a suitable mount, such as an o-ring, 1325. Thus, by rotating the collar 1327, the device 1301 provides a telescoping-type construct. FIG. 13A shows the construct in an extended position; FIG. 13B shows the construct in a fully retracted position. In the extended position of FIG. 13A, the internal chamber 1309 of the housing is substantially enlarged by the volume of cavity 1309' of the movable focusing cone 1333. Water is added via the inlet tubes as the volume of the entire chamber 1309, 1309' increases when the collar 1327 is rotated and withdrawn as the volume decreases when the collar is counter-rotated. Suitable mounting and sealing o-rings 1311, 1313, 1317 and screw 1315 are provided as necessary to complete the device 1301.

As can now be recognized, a telescoping action is produced between the rotatable collar 1327 and the focusing cone member 1333 when the collar 1327 is rotated about its longitudinal axis of rotation, "R-R." Rotating collar 1327 changes the gap, "$F_n$," between the transducer's energy emitting surface 1319 and the acoustic window 1321. As the gap varies, for example from length $F_1$ in FIG. 13A to $F_2$ in FIG. 13B, the depth of focus of the device 1301 varies; distance $F_1$ establishing the deepest focal point or focal zone penetration. As will be recognized by a person skilled in the art, the device's construct is adaptable to a variety of transducer types and size implementations.

Figure 14:
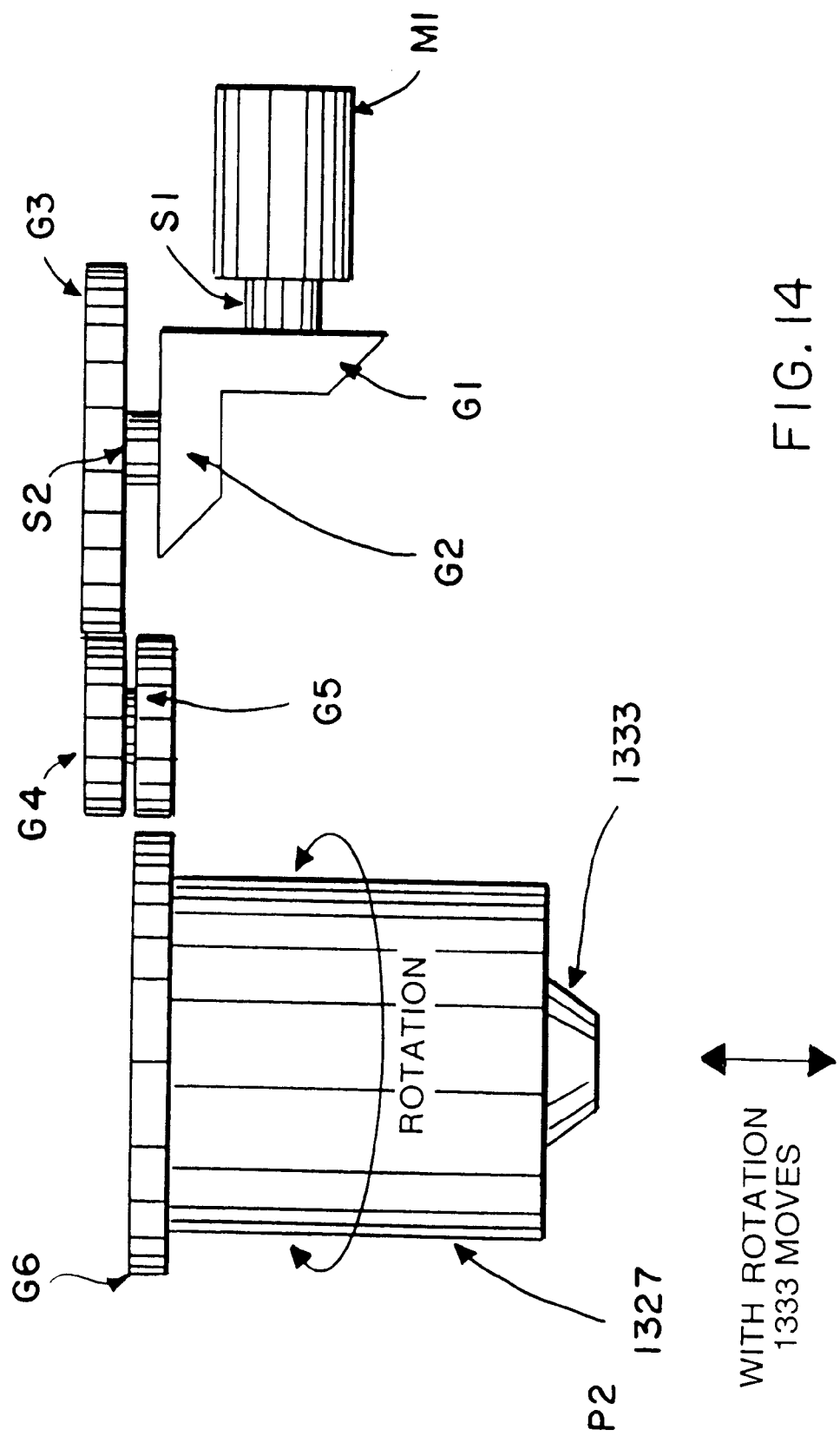
FIG. 14 is an exemplary automated drive system for the apparatus as shown in FIGS. 13A–13B.

The rotating collar may be manually or electro-mechanically rotated. FIG. 14 depicts a schematic for an automated focus dept adjustment system. A motor M1, such as a stepper motor, is coupled by drive shaft S1 to a gear train G1, G2, G3, gear shaft S2, G4, G5 and G6. The rotating collar 1327 is coupled to gear G6 such that by activation of the motor, e.g., via a surgeon operated foot switch (not shown), precise depth of focus can be achieved as focusing cone 1333 moves with rotation as shown by the arrow labeled "With Rotation 1333 Moves". Since the mechanism will necessarily be used under sterile conditions, this configuration allows a single motor and gear train G1–G4 to be enclosed in a sealed section; gear G5 and the combined unit of gear G6 and the transducer system (FIGS. 13A & 13B) within rotating collar 1327 are removable from the shaft for cleaning and sterilization.

Figure 15A:
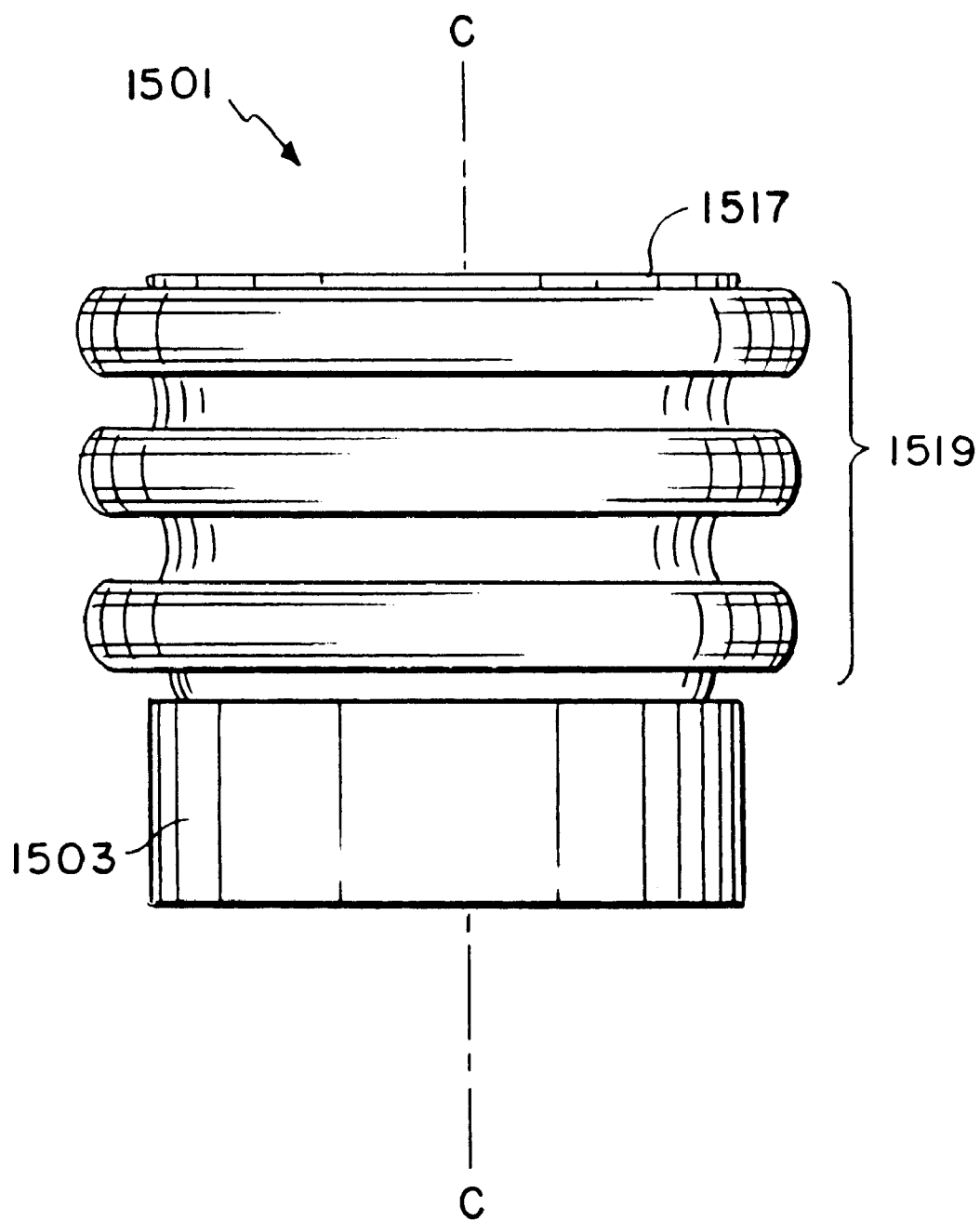
Figure 15B:
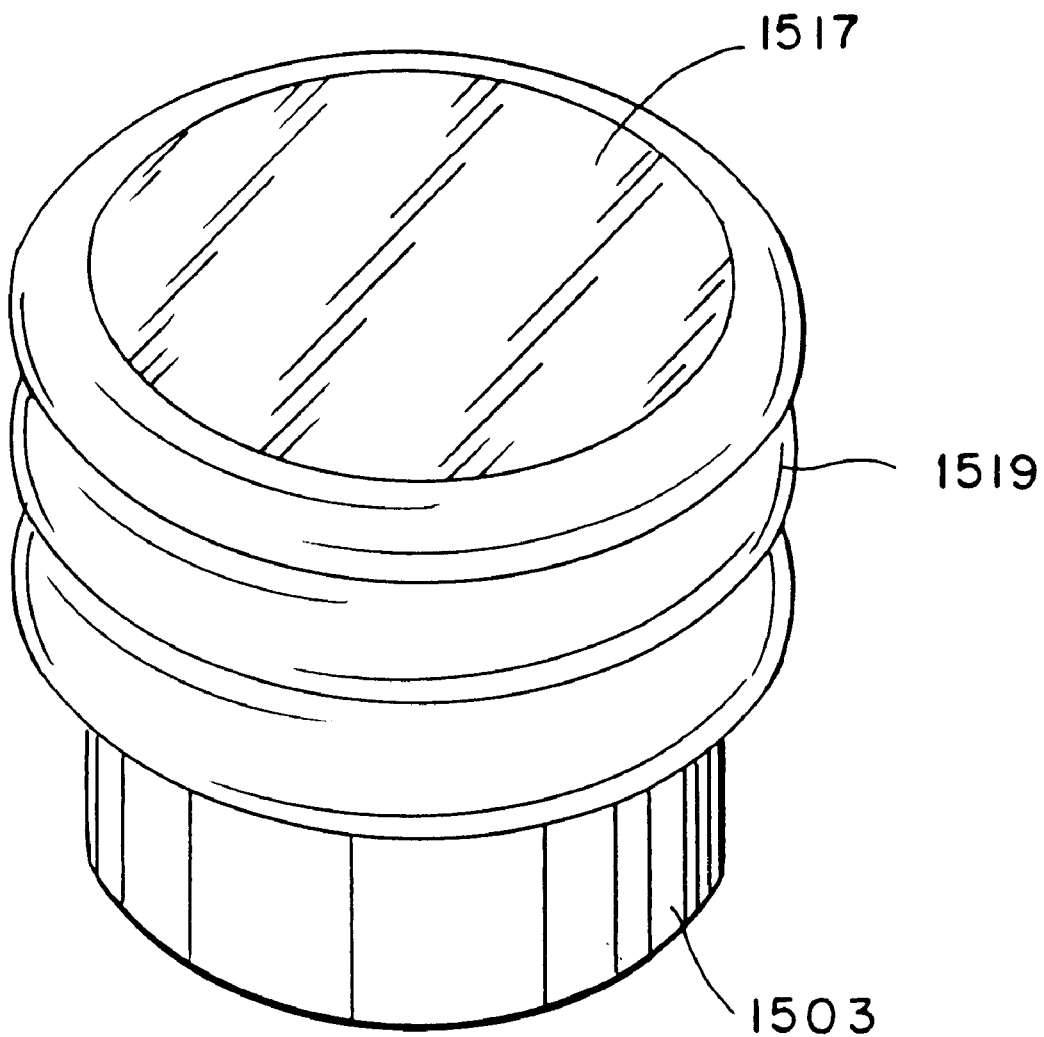
Figure 15C:
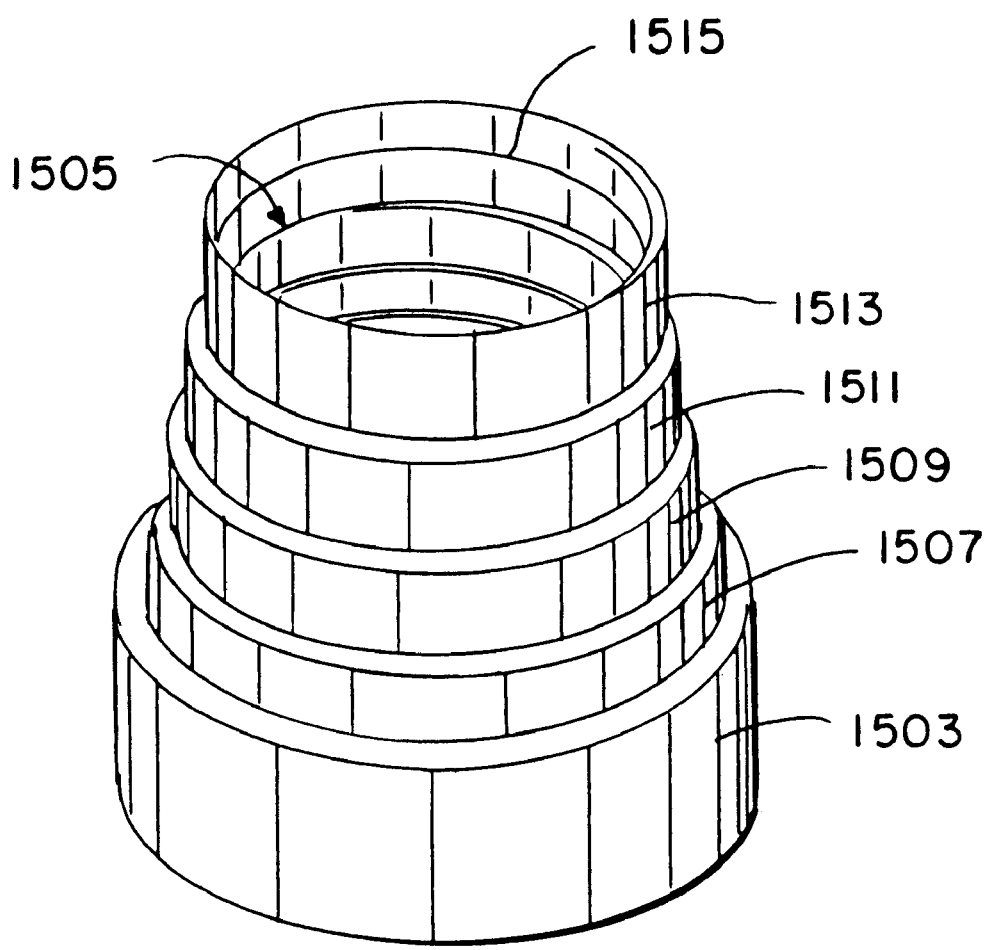

An alternative embodiment of a device 1501 having a focusing mechanism is shown in FIGS. 15A–15C. A base 1503 (similarly, see also FIG. 13A, element 1303) holds a transducer (not shown) projecting inwardly through a cavity 1505, FIG. 15C, of the device. The cavity 1505 is formed by a plurality of telescopic cylinders 1507, 1509, 1511, 1513. The cavity 1505 is adapted for filling with an acoustic coupling fluid, e.g., degassed water. Again, fluid couplings not shown, but as would be obvious to a person skilled in the art, are provided to keep the cavity filled during expansion and contraction. A spring 1515 is mounted inside the cavity to bias against an end plate 1517 (FIGS. 15A & 15B only). A bellows 1519 surrounds the telescopic cylinders 1507–1513 and the end plate 1517 is attached thereto in contact with the spring 1515 and the telescopic cylinders distally from the base 1503. Thus, the device is in an expanded condition unless compressed by pushing the end plate against the tissue to a degree to force the spring and bellows to begin to collapse.

The end plate 1517 is rigid on its circumference for connection to the bellows. The inner radial region of the end plate 1517 may be of a different material, but essentially must be transparent to ultrasonic energy. The purpose of the telescoping sections is to maintain the axial alignment with the center of the axis, C—C, running through the aligned base 1503 and the end plate 1517. Thus, the ultrasound energy emitted by the transducer will not encounter the inner walls of the telescopic cylinders 1507–1513. A flexible bag acoustic coupler 111 lacks this ability.

Note that this embodiment can be adapted for use with either a fixed system as exemplified in FIGS. 1B–5B and 14, or can be hand held as in FIGS. 8A–8C.

Hemostasis Procedures

As another example of the methodology of the present invention, consider traumatic bleeding. For example, uncontrolled hemorrhage of the liver is a primary cause of death in hepatic trauma, occurring in 30% of penetrating and 15–20% of blunt abdominal trauma, with a mortality rate of 10–15%. Abdominal trauma patients are often already in hemorrhagic shock prior to arrival at surgery. Another application is for treating a punctured vessel in a medical situation where a catheter has been removed from the artery, resulting in bleeding. Additionally, emergency rescue teams are often faced with massive bleeding injuries with nothing more than tourniquets to use to stem the flow of blood.

In accordance with the present invention, ultrasound having a frequency in a range of 0.5 MHZ–20 MHz is focused onto the outer regions of the vessel adjacent to where the puncture or tear occurred. The energy level and the duration of exposure is monitored such that the application of HIFU causes the closure of the fibrous sheath surround a vessel without damaging or irreversibly damaging the wall tissue of the vessel itself. [But cf., Potential Adverse Effects of High-intensity Focused Ultrasound Exposure on Blood Vessels In Vivo, Hynynen et al., Ultrasound in Med. & Biol., Vol. 22, No. 2, pp. 193–201, 1996.]

Particularly suited to this process and portable implementations are apparatus such as depicted in FIGS. 7 and 8A–8C since they provide simple, hand-held embodiments. Having a fixed depth of focus immediately adjacent the front of the instrument, makes the embodiment of FIG. 7 particularly useful in a roadside, medical emergency where portability is a factor. Specific instrument design factors, viz., frequency, transducer size, power, and the like as discussed heretofore, will determine the duration of application to cause hemostasis. Again, treatment parameters are device specific and must be determined empirically. As an example, a device similar to the embodiments shown in FIGS. 8A–8B was used for experiments (performed in accordance with the appropriate laws and guidelines of the U.S. Nation Institute of Health for the use of laboratory animals). A HIFU, spherically curved transducer had an aperture of 6.34 $cm^2$, producing a depth of focus at 4 cm. It was operated at 3.3 MHZ, CW, by applying 300 V peako-peak, producing an acoustic power of 65 W, measured with an absorber-type radiation force balance and a spatial peak intensity at the focal region of approximately 3000 $W/cm^2$. For 94% of incisions in rabbit liver, major hemostasis was achieved in a time of less than approximately two minutes of continuous application of HIFU. The average ± standard deviation of the major hemostasis time was 1.4±0.69 minutes. When a large vessel was cut, in approximately 80% of the incisions, complete hemostasis was achieved in a time less than or equal to 3 minutes of continuous HIFU application.

Note that occurrence of trauma to a specific tissue or organ may start bleeding internally. This may produce a hematoma, a shunt between the arterial and venous system caused by an artery punctured or ruptured in close proximity to a ruptured or punctured vein, or bleeding into some noncardiovascular cavity.

While shunts can occur substantially anywhere in the cardiovascular system, yet another medical problem that involves vascular shunts between the arterial and venous system are congenital defects known as arterial-venous ("AV") malformations. AV malformations often occur in the brain and liver. In a shunt, blood flow may be contained to a local region by reason of the adjacent tissue remaining normal or intact. An open.venous pathway provides a pressure release and site for blood to flow from the higher arterial pressure system. Additionally, a shunt can occur between a vessel with higher pressure to a vessel with a lower pressure. Whatever the cause, the medical problem is that normal tissue does not receive proper blood perfusion. Of further difficulty is that AV malformations themselves have a higher tendency to hemorrhage. In a similar manner, HIFU energy is applied to the region where the internal bleeding is detected, that is, specifically to the vessels with the higher pressure from which the blood is leaking. In accordance with the present invention, such shunts or other internal bleeding can be closed without having to disturb or cut through adjacent tissue, occluding the artery feeding the shunt, the shunt itself, or the vein receiving the shunt blood flow. Alternatively, the whole tissue region or malformation of the vessel feeding the shunt, the shunt, and the vessel receiving the shunt is coagulated using HIFU energy, coagulating the specific volume of tissue involved.

The present invention provides a useful method and apparatus for a variety of presurgical and traumatic bleeding applications.

The foregoing description of the preferred and alternative embodiments of the present invention has been presented for purposes of illustration and description. It is not intended to be exhaustive or to limit the invention to the precise form or to exemplary embodiments disclosed. Obviously, many modifications and variations will be apparent to practitioners skilled in this art. Similarly, any process steps described might be interchangeable with other steps in order to achieve the same result. While liver surgery has been discussed at length in an exemplary embodiment, the volume cauterization procedure is applicable to virtually all organ surgery. The embodiment was chosen and described in order to best explain the principles of the invention and its best mode practical application, thereby to enable others skilled in the art to understand the invention for various embodiments and with various modifications as are suited to the particular use or implementation contemplated. It is intended that the scope of the invention be defined by the claims appended hereto and their equivalents.

What is claimed is:

1. A presurgical device for preparing an organ of a patient for surgical incisions, comprising:

transducer means for emitting energy as high frequency focused ultrasound; and means for controlling focal position and focal intensity of energy emissions from said transducer means such that acoustic energy at selective focal zones produces coagulative necrosed tissue in the form of predetermined surgical pathways within the tissue such that surgical incisions along the surgical pathways is subject to substantially no bleeding; and tissue backing means for protecting tissue beyond a selective focal zone from exposure effects of emitted energy from the transducer means.

2. The device as set forth in claim 1, said tissue backing means further comprising:

an acoustic energy absorber having an acoustic impedance approximately equal to acoustic impedance of the tissue at the frequency of the emitted energy and a thickness and thermal properties such that abutting the tissue does not become heated by said absorber.

3. The device as set forth in claim 1, said tissue backing means further comprising:

means for reflecting said emitted energy back to said focal zone.

4. The device as set forth in claim 1, further comprising:

said transducer means emits high intensity focused ultrasound energy having a depth of focus and depth of field in respective ranges in combination with said means for controlling such that the device provides cauterization of visible hemorrhaging.

5. The device as set forth in claim 1, said transducer means further comprises:

said transducer means having at least one surface for emitting acoustic energy having a frequency in the range of 0.5 MHZ to 20 MHz; and mounted to said transducer means, means for acoustically coupling said energy to the tissue, including a liquid-filled chamber mounted proximate said surface and having an acoustic energy window at a position distal from said surface and means for varying gap distance from said surface to said window such that depth of said selective focal zone position changes as said gap distance is increased and decreased using said means for varying gap distance.

6. The device as set forth in claim 5, wherein said means for acoustically coupling further comprises:

a telescoping construct having a fully retracted position providing a shallow tissue penetration depth of focus, a fully extended position providing a predetermined deep tissue penetration depth of focus, and providing a substantially continuous range of depth of focus positions between said shallow tissue penetration depth of focus and said deep tissue penetration depth of focus.

7. The device as set forth in claim 6, said telescoping construct further comprising:

first means for mounting a high intensity focused ultrasound transducer and for providing an acoustic coupling medium chamber adjacent the transducer; and second means for mounting an acoustic window for focusing ultrasound energy emitted by said transducer, wherein said second means is coupled to said first means by a screw-type interface such that a gap between said transducer and said acoustic window is variable such that depth of focus of the ultrasound energy is selected by using said screw-type interface to vary the gap.

8. The device as set forth in claim 6, said telescoping construct further comprising:

first means for mounting a high intensity focused ultrasound transducer and for providing an acoustic coupling medium chamber adjacent the transducer; and second means for mounting an acoustic window for focusing ultrasound energy emitted by said transducer, wherein said second means is coupled to said first means by a bellows-type interface such that a gap between said transducer and said acoustic window is variable such that depth of focus of the ultrasound energy is selected by using said bellows-type interface to vary the gap.

* * * * *